United States Patent
Whitehead et al.

(10) Patent No.: US 6,479,493 B1
(45) Date of Patent: Nov. 12, 2002

(54) METHODS FOR TREATMENT OF TYPE I DIABETES

(75) Inventors: Clark M. Whitehead, Warminster, PA (US); Keith A. Earle, North Wales, PA (US); Hector W. Alila, North Wales, PA (US); W. Joseph Thompson, Doylestown, PA (US)

(73) Assignee: Cell Pathways, Inc., Horsham, PA (US)

( * ) Notice: Subject to any disclaimer, the term of this patent is extended or adjusted under 35 U.S.C. 154(b) by 10 days.

(21) Appl. No.: 09/935,802

(22) Filed: Aug. 23, 2001

(51) Int. Cl.⁷ .......... A61K 31/53; A61K 31/50; A61K 31/47; A61K 31/44; A61K 31/425

(52) U.S. Cl. .......... 514/241; 514/252.1; 514/255.06; 514/307; 514/311; 514/357; 514/365; 514/381; 514/394; 514/400; 514/406; 514/419; 514/427; 514/461; 514/866

(58) Field of Search .......... 514/241, 252.1, 514/255.06, 307, 311, 357, 365, 381, 394, 400, 406, 419, 427, 461, 866

(56) References Cited

U.S. PATENT DOCUMENTS

| | | |
|---|---|---|
| 3,031,450 A | 4/1962 | Fischer et al. |
| 3,161,654 A | 12/1964 | Shen |
| 3,312,730 A | 4/1967 | Winter et al. |
| 3,322,755 A | 5/1967 | Roch et al. |
| 3,325,358 A | 6/1967 | Winter et al. |
| 3,532,752 A | 10/1970 | Shen |
| 3,642,785 A | 2/1972 | Shen et al. |
| 3,647,858 A | 3/1972 | Hinkley et al. |
| 3,654,349 A | 4/1972 | Shen et al. |
| 3,692,651 A | 9/1972 | Sletzinger et al. |
| 3,692,825 A | 9/1972 | Conn |
| 3,737,455 A | 6/1973 | Shen et al. |
| 3,851,063 A | 11/1974 | Shen et al. |
| 3,860,636 A | 1/1975 | Shen et al. |
| 4,307,114 A | 12/1981 | Dvornik et al. |
| 4,402,979 A | 9/1983 | Shen et al. |
| 4,423,074 A | 12/1983 | Dvornik et al. |
| 4,423,075 A | 12/1983 | Dvornik et al. |
| 4,880,810 A | 11/1989 | Lowe, III |
| 4,885,301 A | 12/1989 | Coates |
| 5,298,525 A | 3/1994 | Yoon et al. |
| 5,401,774 A | 3/1995 | Pamukcu et al. |
| 5,470,873 A | 11/1995 | Yoon |
| 5,488,055 A | 1/1996 | Kumar et al. |
| 5,527,896 A | 6/1996 | Wigler et al. |
| 5,602,019 A | 2/1997 | Beavo et al. |
| 5,602,171 A | 2/1997 | Tang et al. |
| 5,614,530 A | 3/1997 | Kumar et al. |
| 5,614,627 A | 3/1997 | Takase et al. |
| 5,708,022 A | 1/1998 | Bastos et al. |
| 5,776,752 A | 7/1998 | Beavo et al. |
| 5,789,553 A | 8/1998 | Beavo et al. |
| 5,798,374 A | 8/1998 | Tang et al. |
| 5,800,987 A | 9/1998 | Beavo et al. |
| 5,852,035 A | 12/1998 | Pamukcu et al. |
| 5,858,694 A | 1/1999 | Piazza et al. |
| 5,861,396 A | 1/1999 | Nieöhner et al. |
| 5,874,440 A | 2/1999 | Pamukcu et al. |
| 5,883,110 A | 3/1999 | Tang et al. |
| 5,885,834 A | 3/1999 | Epstein |
| 5,902,827 A | 5/1999 | Pamukcu et al. |
| 5,922,595 A | 7/1999 | Fisher et al. |
| 5,942,520 A | 8/1999 | Pamukcu et al. |
| 5,948,911 A | 9/1999 | Pamukcu et al. |
| 5,958,982 A | 9/1999 | Pamukcu et al. |
| 5,990,117 A | 11/1999 | Pamukcu et al. |
| 5,998,463 A | 12/1999 | Hulin et al. |
| 6,008,215 A | 12/1999 | Flockerzi |
| 6,015,677 A | 1/2000 | Beavo et al. |
| 6,034,099 A | 3/2000 | Pamukcu et al. |
| 6,037,345 A | 3/2000 | Pamukcu et al. |
| 6,046,199 A | 4/2000 | Pamukcu et al. |
| 6,046,206 A | 4/2000 | Pamukcu et al. |
| 6,046,216 A | 4/2000 | Piazza et al. |
| 6,060,477 A | 5/2000 | Piazza et al. |
| 6,063,818 A * | 5/2000 | Sperl et al. ............. 514/622 |
| 6,066,634 A * | 5/2000 | Sperl et al. ............. 514/241 |

(List continued on next page.)

FOREIGN PATENT DOCUMENTS

| | | |
|---|---|---|
| EP | 0 349 239 A2 | 1/1990 |
| EP | 0 395 328 A2 | 10/1990 |
| EP | 0 428 268 A2 | 5/1991 |
| EP | 0 463 756 A1 | 1/1992 |
| EP | 0 293 063 B1 | 3/1992 |
| EP | 0 526 004 A1 | 2/1993 |
| EP | 0 351 058 B1 | 6/1993 |
| EP | 0 347 146 B1 | 9/1993 |
| EP | 0 352 960 B1 | 10/1994 |
| EP | 0 722 943 A1 | 1/1996 |
| EP | 0 722 944 A1 | 1/1996 |
| EP | 1 074 258 A3 | 4/2001 |
| GB | 807826 | 1/1959 |
| GB | 2 063 249 A | 6/1981 |

OTHER PUBLICATIONS

Ahmad F. et al., IL–3 ad IL–4 Activate Cyclic Nucleotide Phosphodiesterases 3 (PDE3) and 4 (PDE4) by Different Mechanisms in FDCP2 Myeloid Cells, J. Immunology vol. 162, Part 8, pp. 4864–4875 (Apr. 15, 1999).*

Boven LA et al., Macrophage inflammatory protein–1 alpha (MIP–1alpha), MIP–1beta, and RANTES mRNA semiquantification and protein expression in active demyelinating multiple sclerosis (MS) lesions, *Clin. Exp. Immunol.* 2000 Nov.; 122(2):257–63 (Abstract Only).*

(List continued on next page.)

*Primary Examiner*—Kevin E. Weddington
(74) *Attorney, Agent, or Firm*—Robert W. Stevenson

(57) ABSTRACT

Substituted condensation products of -benzyl-3-indenylacetamides with heterocyclic aldehydes and other such inhibitors are useful for the treatment of type I diabetes.

40 Claims, 16 Drawing Sheets

(11 of 16 Drawing Sheet(s) Filed in Color)

U.S. PATENT DOCUMENTS

| | | | |
|---|---|---|---|
| 6,069,240 | A | 5/2000 | Wigler et al. |
| 6,071,934 | A | 6/2000 | Sperl et al. |
| 6,077,842 | A | 6/2000 | Pamukcu et al. |
| 6,080,540 | A | 6/2000 | Wigler et al. |
| 6,080,742 | A | 6/2000 | Germann et al. |
| 6,080,772 | A | 6/2000 | Tang et al. |
| 6,100,025 | A | 8/2000 | Wigler et al. |
| 6,107,295 | A | 8/2000 | Rochus et al. |
| 6,124,303 | A | 9/2000 | Pamukcu et al. |
| 6,133,271 | A | 10/2000 | Pamukcu et al. |
| 6,143,746 | A | 11/2000 | Daugan et al. |
| 6,143,759 | A | 11/2000 | Flockerzi |
| 6,143,765 | A | 11/2000 | Tang et al. |
| 6,143,777 | A | 11/2000 | Jonas et al. |
| 6,169,090 | B1 | 1/2001 | Dyke et al. |
| 6,174,884 | B1 | 1/2001 | Haning et al. |
| 6,187,779 | B1 | 2/2001 | Pamukcu et al. |
| 6,200,771 | B1 | 3/2001 | Liu et al. |
| 6,200,980 | B1 | 3/2001 | Piazza et al. |
| 6,207,666 | B1 | 3/2001 | Piazza et al. |
| 6,211,177 | B1 | 4/2001 | Sperl et al. |
| 6,211,220 | B1 | 4/2001 | Pamukcu et al. |
| 6,232,312 | B1 | 5/2001 | Pamukcu et al. |
| 6,235,742 | B1 | 5/2001 | Bell et al. |
| 6,235,776 | B1 | 5/2001 | Pamukcu et al. |
| 6,235,782 | B1 | 5/2001 | Pamukcu et al. |
| 6,239,136 | B1 | 5/2001 | Pamukcu et al. |
| 6,251,904 | B1 | 6/2001 | Bunnage et al. |
| 6,255,303 | B1 | 7/2001 | Sterk et al. |
| 6,255,456 | B1 | 7/2001 | Fisher et al. |
| 6,258,833 | B1 | 7/2001 | Martins et al. |
| 6,268,372 | B1 | 7/2001 | Pamukcu et al. |

FOREIGN PATENT DOCUMENTS

| | | |
|---|---|---|
| JP | SHO 61-106521 | 5/1986 |
| JP | Hei 8-311035 | 11/1996 |
| WO | WO 93/07149 | 4/1993 |
| WO | WO 94/29277 | 11/1994 |
| WO | WO 97/03675 | 2/1997 |
| WO | WO 97/03985 | 2/1997 |
| WO | WO 97/24334 | 7/1997 |
| WO | WO 98/06722 | 2/1998 |
| WO | WO 98/14448 | 4/1998 |
| WO | WO 98/17668 | 4/1998 |
| WO | WO 98/19679 A1 | 5/1998 |
| WO | WO 99/65880 | 11/1999 |
| WO | WO 00/12501 | 3/2000 |
| WO | WO 00/23091 | 4/2000 |
| WO | WO 00/26201 | 5/2000 |
| WO | WO 00/26208 | 5/2000 |
| WO | WO 00/27861 | 5/2000 |
| WO | WO 00/42017 | 7/2000 |
| WO | WO 00/42018 | 7/2000 |
| WO | WO 00/42019 | 7/2000 |
| WO | WO 00/42034 | 7/2000 |
| WO | WO 00/59890 | 10/2000 |
| WO | WO 00/64424 | 11/2000 |
| WO | WO 01/04099 A1 | 1/2001 |

OTHER PUBLICATIONS

Cooper N. et al., A comparison of the inhibitory activity of PDE4 inhibitors on leukocyte PDE4 activity in vitro and eosinophil trafficking in vivo, British Journal of Pharmacology (1999) 126, pp. 1863–1871.*

Czirjak L. et al., Investigation of the alveolar macrophages and T lymphocytes in 15 patients with systemic sclerosis, Clin Rheumatology 1999; 18(5), pp. 357–363 (Abstract Only).*

Danahay H. et al., PDE4 inhibition and a corticosteroid in chronically antigen exposed conscious guinea–pigs, Clinical and Experimental Allergy, 1998, vol. 28, pp. 513–522.*

Duggan, D.E. et al., Identification of the Biologically Active Form of Sulindac, J. Pharm. & Exper. Therap., vol. 201, No. 1, pp. 8–13 (1977).*

Gantner F. et al., Characterization of the Phosphodiesterase (PDE) Pattern of in Vitro–Generated Human Dendritic Cells (DC) and the Influence of PDE Inhibitors on CD Function, Pulmonary Pharmacology & Therapeutics (1999) 12, pp. 377–386.

Gantner F. et al., In vitro differentiation of human monocytes to macrophages: change of PDE profile and its relationship to suppression of tumour necrosis factor–α release by PDE inhibitors, British Journal of Pharmacology (1997) 121, pp. 221–231.

Gehrmann J. et al., Amyloid precursor protein (APP) expression in multiple sclerosis lesions, Glia 1995 Oct.;15(2), pp. 141–151 (Abstract Only).

Germain N. et al., Selective phosphodiesterase inhibitors modulate the activity of alveolar macrophages from sensitized guinea–pigs, Eur. Respir. J. 1998:12, pp. 1334–1339.

Giembycz, M.A., Phosphodiesterase 4 Inhibitors and the Treatment of Asthma, Drugs 2000 Feb.: 59(2), pp. 193–212.

Gonzaga, R.A.F. et al., The Lancet, Mar. 30, 1985, p. 751.

Hammermann, R. et al., Phosphodiesterase Inhibitors and Forskolin Up–regulate Arginase Activity in Rabbit Alveolar Macrophages Pulmonary Pharmacology and Therapeutics 2000; vol. 13, No. 3, pp. 141–147.

He W. et al., Novel Cyclic Compounds as Potent Phosphodiesterase 4 Inhibitors, J. Med. Chem., vol. 41, Part 22, pp. 4216–4223 (Oct. 22, 1998).

Hollander AP et al., Expression of hypoxia–inducible factor 1 alpha by macrophages in the rheumatoid synovium: implications for targeting of therapeutic gene to the inflamed joint, Arthritis Rheum. 2001 Jul.; 44(7): 1540–4 (Abstract Only).

Imahashi K. et al., Type IV Phosphodiesterase Inhibitor Suppresses Insulin–Dependent Myocarcial Glucose Uptake, Clin Exp Pharmacol Physiol 2001 Apr.; 28(4), pp. 290–291 (Abstract Only).

Ishikawa O. et al., Macrophage infiltration in the skin of patients with systemic sclerosis, J. Rheumatology 1992 Aug.; 19(8), pp. 1202–1206 (Abstract Only).

Kapur S. et al., Expression of Nitric Oxide Synthase in Skeletal Muscle, Diabetes, vol. 46, Nov. 1997, pp. 1691–1700.

Kelly J. et al., Characterization of phosphodiesterase 4 in guinea–pig macrophages: multiple activities, association states and sensitivity to selective inhibitors, British Journal of Pharmacology (1998) 124, pp. 129–140.

Kelly J. et al., Phosphodiesterase 4 in macrophages: relationship between cAMP accumulation, suppresion of cAMP hydrolysis and inhibition of [$^3$H]R–(–)–rolipram binding by selective inhibitors, Biochem. J. (1996) 318, pp. 425–436.

Kumar A. et al., Analgesic and anti–inflammatory effects of phosphodiesterase inhibitors, Indian J Exp Biol 2000 Jan.;38(1), pp. 26–30 (Abstract Only).

Lee MS et al., A comparative immunohistochemical study of lichen planus and discoid lupus erythematosus, Australas Jj. Dermatol. 1996 Nov.; 37(4): 188–92 (Abstract Only).

McPherson M.A. et al., A cyclic nucleotide PDE5 inhibitor corrects defective mucin secretion in submandibular cells containing antibody directed against the cystic fibrosis transmembrane conductance regulator protein, FEBS Letters 464 (1999), pp. 48–52.

Mery P.F. et al., Erythor–9–(2–hydroxy–3–nonyl)adenine inhibits cyclic GMP–stimulated phosphodiesterase in isolated cardiac myocytes, Mol. Pharmacology 1995 Jul.;48(1), pp. 121–130 (Abstract Only).

Méry, Pierre–Francois et al., EHNA as an inhibitor of PDE2: A Pharmacological and Biochemical Study in Cardiac Myocytes, Phosphodiesterase Inhibitors (1996), pp. 81–88.

Michie, A.M. et al., Rapid regulation of PDE–2 and PDE–4 cyclic AMP phosphodiesterase activity following ligation of the T cell antigen receptor on thymocytes: analysis using the selective inhibitors erytrho–9–(2–hydroxy–3–nonyl)–adenine (EHNA) and rolipram, Cell Signal 1996 Feb.;8(2), pp. 97–110.

Niebauer J. et al., Local L–Arginine Delivery After Balloon Angioplasty Reduces Monocyte Binding and Induces Apoptosis, Circulation 1999:100, pp. 1830–1835.

Odoux C. et al., Endothelin–1 secretion by alveolar macrophages in sytemic sclerosis, Am. J. Respir. Crit. Care Med. 1997 Nov.;156(5), pp. 1429–1435 (Abstract Only).

Ostensen M. et al., Nonsteroidal anti–inflammatory drugs in systemic lupus erythematosus, Lupus (2001) 10, pp. 135–139.

Piazza G.A. et al., Antineoplastic Drugs Sulindac Sulfide and Sulfone Inhibit Cell Growth by Inducing Apoptosis, Cancer Research 55, Jul. 15, 1995, pp. 3110–3116.

Reis E. et al., Sulindac inhibits neointimal formation after arterial injury in wild–type and apolipoprotein E–deficient mice, PNAS 97(23): pp. 12764–12769.

Rice P.L. et al., Inhibition of extracellular signal–regulated kinase 1/2 phosphorylation and induction of apoptosis by sulindac metabolites, Cancer Research 2001, Feb 15;61(4), pp. 1541–1547 (Abstract Only).

Soh, Jae–Won et al., Cyclic GMP Mediates Apoptosis Induced by Sulindac Derivatives via Activation of c–Jun $NH_2$–Terminal Kinase 1, Clinical Cancer Research vol. 6, pp. 4136–4141, Oct. 2000.

Soh, Jae–Won et al., Protein Kinase G Activates the JNK1 Pathway via Phsophorylation of MEKK1, The Journal of Biological Chemistry, vol. 276, No. 19, pp. 16406–16410 (2001).

Thompson, W.J. et al., Exisulind Induction of Apoptosis Involves Guanosine 3',5'–Cyclic Monophosphate Phosphodiesterase Inhibition, Protein Kinase G Activation, and Attenuated β–Catenin, Cancer Research 60, pp. 3338–3342, Jul. 1, 2000.

Tien, Xiao–Ying, et al., Activation of the Cystic Fibrosis Transmembrane Conductance Regulator by cGMP in the Human Colonic Cancer Cell Line, Caco–2, The Journal of Biological Chemistry, vol. 269, No. 1, pp. 51–54 (1994).

Tsukahara T et al., Cytophagic histiocytic panniculitis in systemic lupus erythematosus, *Hiroshima J. Med. Sci.*, 1995 Mar.; 44(1): 13–6 (Abstract Only).

Waddel W. R. et al., Sulindac for Polyposis of the Colon, The American Journal of Surgery, vol. 157, Jan. 1989, pp. 175–179.

Waddel W.R. et al., Sulindac for Polyposis of the Colon, Journal of Surgical Oncology, 24:pp. 83–87 (1983).

Weyand CM and Goronzy JJ, HLA polymorphisms and T cells in rheumatoid arthritis, *Int. Rev. Immunol.* 1999; 19(1–2):37–39 (Abstract Only).

Wilder R.L. et al., Hormonal regulation of tumor necrosis factor–alpha, interleukin–12 and interleukin–10 production by activated macrophages. A disease–modifying mechanism in rheumatoid arthritis and systemic lupus erythematosus?, Ann. NY Acad. Sci 1999 Jun. 22;876, pp. 14–31 (Abstract Only).

* cited by examiner

U937 mRNA Levels

U937 control PDE3

U937 5nm TPA 24hrs PDE3

U937 Control PDE2

U937 TPA 5nM 24hrs PDE2 cGMP and cAMP Hydrolysis in Permeablized U937 Cells

U937 cells treated with 1 μM compound 38. Apoptotic cells with active caspase 3 label red. Nuclear DNA label blue with DAPI.

Untreated U937 control cells. Apoptotic cells with active caspase 3 label red. Nuclear DNA label blue with DAPI.

U937 cells treated with 0.5uM Rolipram. Apoptotic cells with active caspase 3 label red. Nuclear DNA label blue with DAPI.

U937 cells treated with 0.3nM Sildenafil. Apoptotic cells with active caspase 3 label red. Nuclear DNA label blue with DAPI.

TNFα media levels from U937 cells with or without compound 38 treatment.

METHODS FOR TREATMENT OF TYPE I DIABETES

TECHNICAL FIELD

This invention relates to the treatment of type I diabetes.

BACKGROUND OF THE INVENTION

Type 1 or Insulin Dependent Diabetes Mellitus (IDDM) is estimated to affect 675,000 people in the United States. This represents 0.3% of the total U.S. population, with an estimated 30,000 new cases diagnosed each year. Complications of diabetes impair the longevity and quality of life, and include atherosclerotic heart disease, gangrene and stroke, as well as diabetic retinopathy, neuropathy and nephropathy. Within 15 years after the onset of diabetes, retinopathy may be observed in 97% of Type 1 diabetics. Today diabetic retinopathy remains the leading cause of blindness in the U.S. and patients with diabetes are 25 times more likely to develop blindness than the general population.

Symptoms of diabetic neuropathy have been observed in 54% of Type 1 patients studied. Patients present with symptoms ranging from peripheral sensory-deficits (pins and needles/carpal tunnel syndrome) to autonomic neuropathy resulting in bladder and bowel dysfunction. Type 1 diabetes is also responsible for a large proportion of the patients on renal dialysis, the result of diabetes-induced end stage renal disease. More than 40% of Type 1 patients who have had diabetes for more than 20 years have diabetic nephropathy. The prevalence of myocardial infarction, angina and stroke is 2–3 times greater than in non-diabetics, and the Type 1 diabetic's life span is shortened by about 15 years. The estimated total cost of Type 1 diabetes in the United States (medical expenses, lost wages etc.) is greater than $20 billion per year.

Type I diabetes actually begins before the clinical manifestations of the disease. It starts with the progressive destruction of beta cells in the pancreas. These cells normally produce insulin. The reduction of insulin response to glucose can be measured during this period, however. Ultimately there is massive (>90%) destruction of beta cells in the islets of Langer hans. During the early stages of the disease and beyond, type I diabetes is characterized by the infiltration of pancreatic islets by macrophages and lymphocytes (helper and killer). The macrophage infiltration is believed to prompt the infiltration of small lymphocytes. While clinicians understand the potential for a drug that can address macrophage involvement early in the disease, no safe therapies have yet been found. Current treatment involves daily frequent injections of insulin. However, this can lead to side effects such as hypoglycemic shock.

Thus, there is an urgent, unmet need for safe and effective drug therapies for type I diabetes, particularly a therapy that can intervene in the early stages of the disease to treat macrophage infiltration and prevent subsequent beta cell damage by macrophages.

SUMMARY OF THE INVENTION

This invention represents a novel therapy for treating patients (e.g., humans or companion animals) with type I diabetes without the substantial side effects of prior pharmaceutical approaches. Specifically, this invention involves the administration of an inhibitor of phosphodiesterase 2 ("PDE2") to a mammal in need of treatment for type I diabetes. Preferably, that inhibitor also inhibits phosphodiesterase 5 ("PDE5"). In narrower aspects of this invention, this invention involves the administration of compounds of Formula I below to a mammal in need of treatment for type I diabetes.

As explained below, compounds that inhibit PDE2 can cause activated macrophages to undergo apoptosis.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 13b is a photomicrograph of a regional islet zone in a BBDRJWor rat (diabetic resistant) pancreatic section (arrow). This section is from an aged-matched control for FIG. 13a.

FIG. 14b is a photomicrograph of a regional islet zone in a BBDR/Wor rat (diabetic resistant) pancreatic section (arrow). This section is from an aged-matched control for FIG. 14a.

FIG. 15b is a photomicrograph of a regional islet zone in a BBDR/Wor rat (diabetic resistant) pancreatic section (arrow). This section is from an aged-matched control for FIG. 15a.

DETAILED DESCRIPTION OF THE INVENTION

Figure 1:
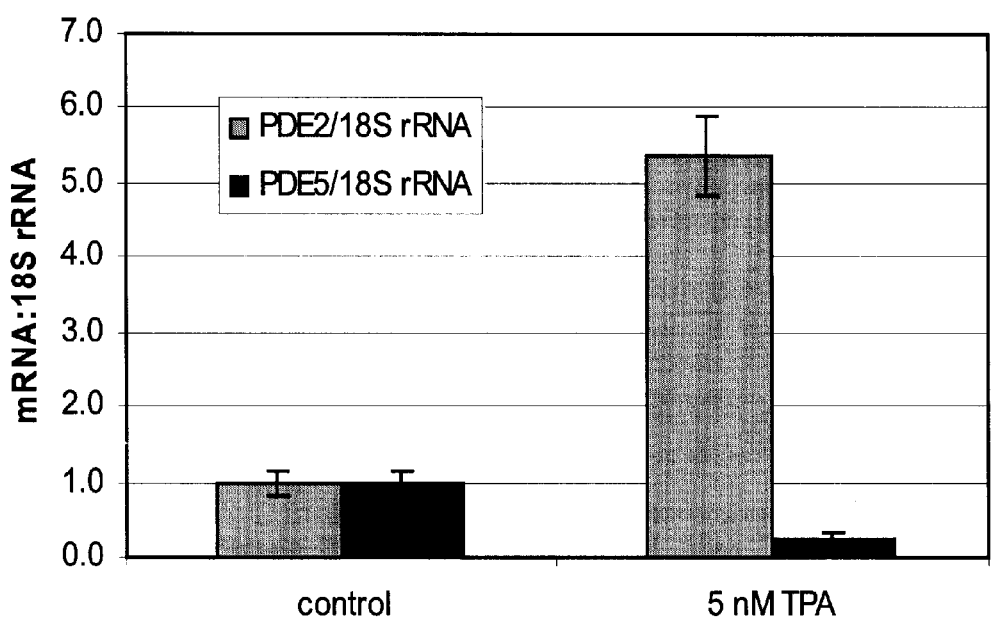
FIG. 1 is a graph that compares the PDE2 and PDE5 MRNA levels in control and activated macrophages.
Figure 2:
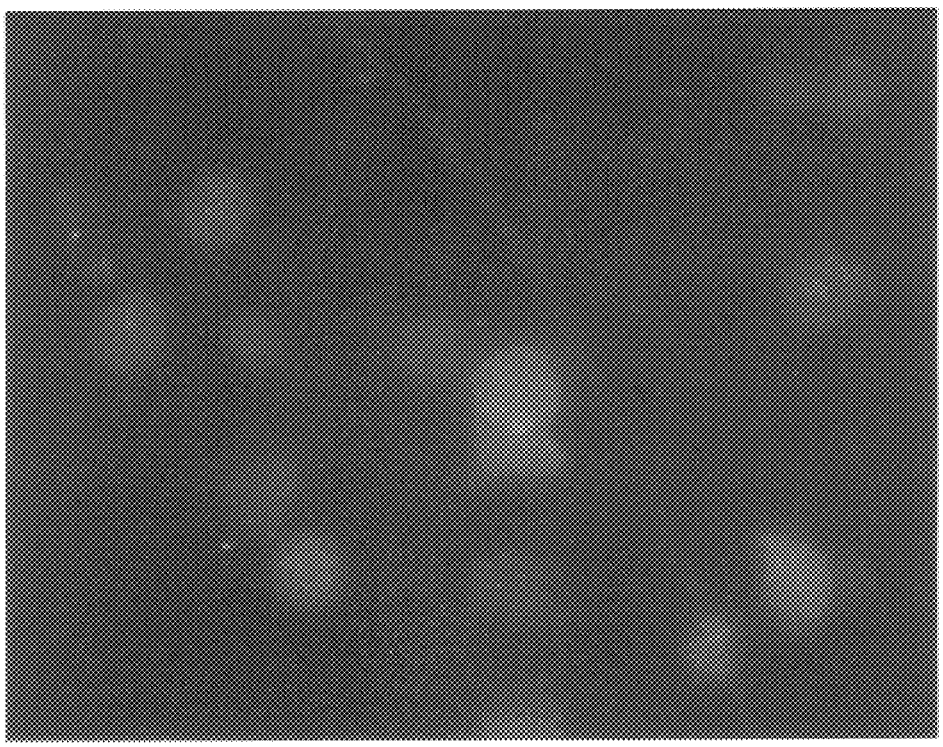
FIG. 2 is a fluorescent microscope photomicrograph of control macrophages stained via indirect immunofluorescence to show basal level of PDE5 protein in the cells.
Figure 3:
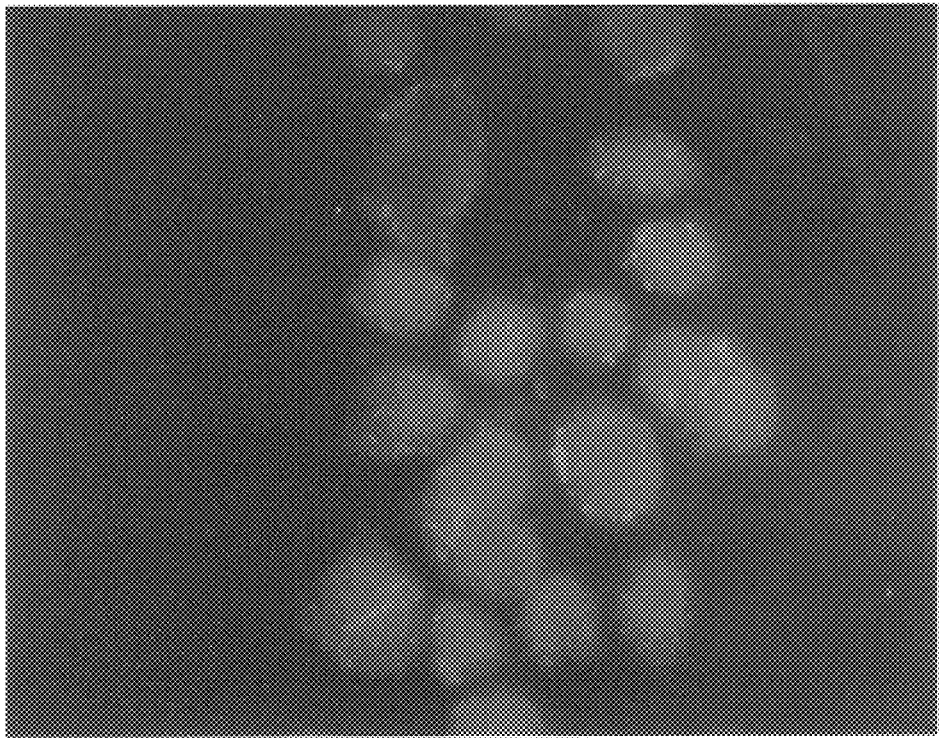
FIG. 3 is a fluorescent microscope photomicrograph of activated macrophages stained via indirect immunofluorescence to show increased level of PDE5 protein in the cells.
Figure 4:
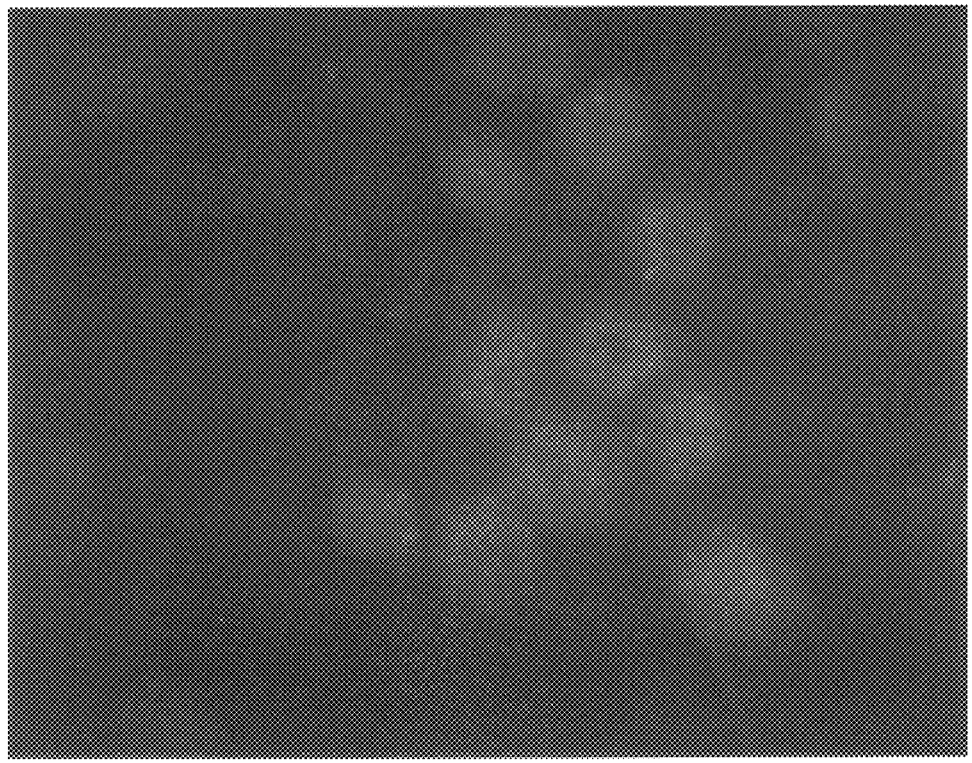
FIG. 4 is a fluorescent microscope photomicrograph of control macrophages stained via indirect immunofluorescence to show basal level of PDE2 protein in the cells.
Figure 5:
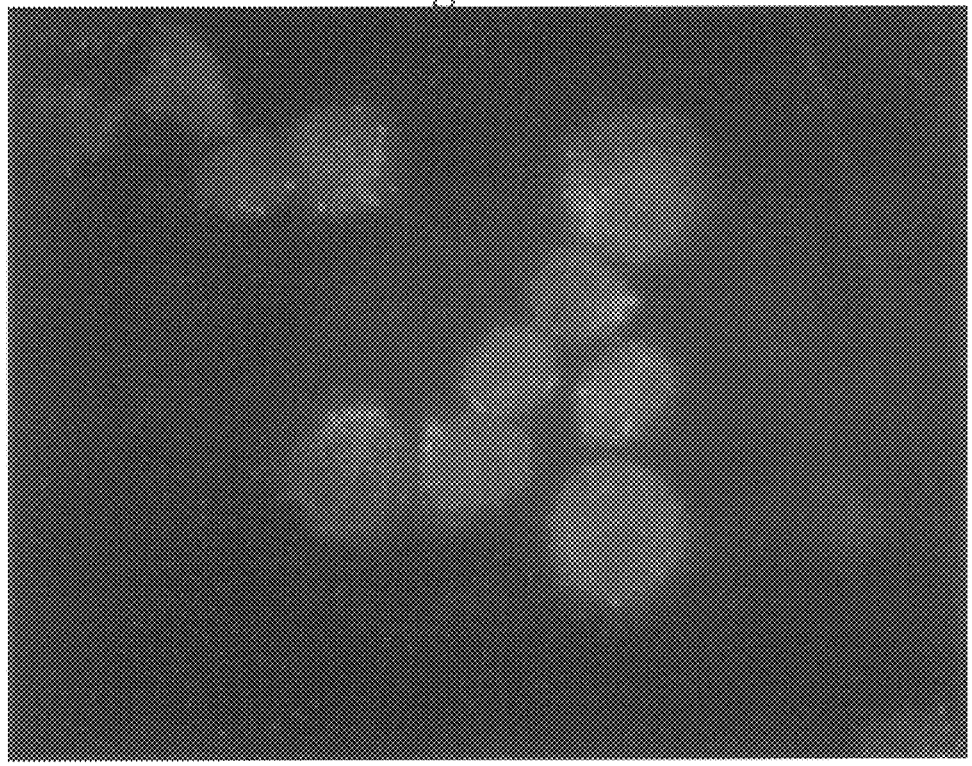
FIG. 5 is a fluorescent microscope photomicrograph of activated macrophages stained via indirect immunofluorescence to show increased level of PDE2 protein in the cells.

As discussed above, the present invention includes the administration of an inhibitor of PDE2 to a mammal in need of treatment for type I diabetes. In addition, this invention includes the use of compounds of Formula I below (as well as their pharmaceutically acceptable salts) for treating a mammal with type I diabetes:

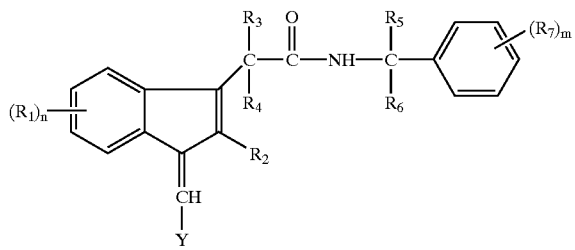

I wherein $R^1$ is independently selected in each instance from the group consisting of hydrogen, halogen, lower alkyl, lower alkoxy, amino, lower alkylamino, di-lower alkylamino, lower alkylmercapto, lower alkyl sulfonyl, cyano, carboxamide, carboxylic acid, mercapto, sulfonic acid, xanthate and hydroxy; $R_2$ is selected from the group consisting of hydrogen and lower alkyl;

$R_3$ is selected from the group consisting of hydrogen, halogen, amino, hydroxy, lower alkyl amino, and di-loweralkylamino;

$R_4$ is hydrogen, or $R_3$ and $R_4$ together are oxygen;

$R_5$ and $R_6$ are independently selected from the group consisting of hydrogen, lower alkyl, hydroxy-substituted lower alkyl, amino lower alkyl, lower alkylamino-lower alkyl, lower alkyl amino di-lower alkyl, lower alkyl nitrile, —$CO_2H$, —$C(O)NH_2$, and a $C_2$ to $C_6$ amino acid;

$R_7$ is independently selected in each instance from the group consisting of hydrogen, amino lower alkyl, lower alkoxy, lower alkyl, hydroxy, amino, lower alkyl amino, di-lower alkyl amino, halogen, —$CO_2H$, —$SO_3H$, —$SO_2NH_2$, and —$SO_2$(lower alkyl);

m and n are integers from 0 to 3 independently selected from one another;

Y is selected from the group consisting of quinolinyl, isoquinolinyl, pyridinyl, pyrinidiyl, pyrazinyl, imidazolyl, indolyl, benzimidazolyl, triazinyl, tetrazolyl, thiophenyl, furanyl, thiazolyl, pyrazolyl, or pyrrolyl, or subsituted variants thereof wherein the substituents are one or two selected from the group consisting of halogen, lower alkyl, lower alkoxy, amino, lower alkylamino, di-lower alkylamino, hydroxy, —$SO_2$(lower alkyl) and —$SO_2NH_2$.

Preferred compounds of this invention for use with the methods described herein include those of Formula I where:

$R_1$ is selected from the group consisting of halogen, lower alkoxy, amino, hydroxy, lower alkylamino and di-loweralkylamino, preferably halogen, lower alkoxy, amino and hydroxy;

$R_2$ is lower alkyl;

$R_3$ is selected from the group consisting of hydrogen, halogen, hydroxy, amino, lower alkylamino and di-loweralkylamino, preferably, hydrogen, hydroxy and lower alkylamino;

$R_5$ and $R_6$ are independently selected from the group consisting of hydrogen, hydroxy-substituted lower alkyl, amino lower alkyl, lower alkylamino-lower alkyl, lower alkyl amino di-lower alkyl, —$CO_2H$, —$C(O)NH_2$; preferably hydrogen, hydroxy-substituted lower alkyl, lower alkyl amino di-lower alkyl, —$CO_2H$, and —$C(O)NH_2$;

$R_7$ is independently selected in each instance from the group consisting of hydrogen, lower alkoxy, hydroxy, amino, lower alkyl amino, di-lower alkyl amino, halogen, —$CO_2H$, —$SO_3H$, —$SO_2NH_2$, and —$SO_2$(lower alkyl); preferably hydrogen, lower alkoxy, hydroxy, amino, amino lower alkyl, halogen, —$CO_2H$, —$SO_3H$, —$SO_2NH_2$, and —$SO_2$(lower alkyl);

Preferably, at least one of the $R_7$ substituents is para- or ortho-located; most preferably ortho-located;

Y is selected from the group consisting of quinolinyl, isoquinolinyl, pyridinyl, pyrimidinyl and pyrazinyl or said substituted variants thereof.

Preferably, the substituents on Y are one or two selected from the group consisting of lower alkoxy, amino, lower alkylamino, di-lower alkylamino, hydroxy, —$SO_2$(lower alkyl) and —$SO_2NH_2$; most preferably lower alkoxy, di-lower alkylamino, hydroxy, —$SO_2$(lower alkyl) and —$SO_2NH_2$.

The present invention also is a method of treating a mammal with type I diabetes by administering to a patient a pharmacologically effective amount of a pharmaceutical composition that includes a compound of Formula I, wherein $R_1$ through $R_7$ and Y are as defined above. Preferably, this composition is administered without therapeutic amounts of an NSAID.

Compounds of this invention are inhibitors of phosphodiesterases PDE2. For convenience, the PDE inhibitory activity of such compounds can be tested as taught in U.S. patent application Ser. No. 09/046,739 filed Mar. 24, 1998 to Pamukcu et al., which is incorporated herein by reference. Thus, compounds employed in this invention are useful inhibitors of PDE2 and preferably also PDE5. Most preferably, such compounds have an IC50 for PDE2 of no more than 25 μM.

Additional compounds besides those of Formula I can be identified for inhibitory effect on the activity of PDE2 and/or PDE5. Alternatively, cyclic nucleotide levels in whole cells are measured by radioimmunoassay ("RIX") and compared to untreated and drug-treated tissue samples and/or isolated enzymes.

Phosphodiesterase activity can be determined using methods known in the art, such as a method using radioactive $^3$H cyclic GMP (cGMP)(cyclic 3',5'-guanosine monophosphate) as the substrate for the PDE enzyme. (Thompson, W. J., Teraski, W. L., Epstein, P. M., Strada, S. J., *Advances in Cyclic Nucleotide Research*, 10:69–92, 1979, which is incorporated herein by reference). In brief, a solution of defined substrate $^3$H-cGMP specific activity (0.2 μM; 100,000 cpm; containing 40 mM Tris-HCl (pH 8.0), 5 mM MgCl$_2$ and 1 mg/mL BSA) is mixed with the drug to be tested in a total volume of 400 μl. The mixture is incubated at 30° C. for 10 minutes with isolated PDE2 and/or PDE5. Reactions are terminated, for example, by boiling the reaction mixture for 75 seconds. After cooling on ice, 100 μl of 0.5 mg/mL snake venom (O. Hannah venom available from Sigma) is added and incubated for 10 minutes at 30° C. This reaction is then terminated by the addition of an alcohol, e.g. 1 mL of 100% methanol. Assay samples are applied to 1 mL Dowex 1-X8 column; and washed with 1 mL of 100% methanol. The amount of radioactivity in the breakthrough and the wash from the column is combined and measured with a scintillation counter. The degree of phosphodiesterase inhibition is determined by calculating the amount of radioactivity in drug-treated reactions and comparing against a control sample (a reaction mixture lacking the tested compound but with drug solvent).

Alternatively, the ability of desirable compounds to inhibit the phosphodiesterases of this invention is reflected by an increase in cGMP in type I diabetes (pancreatic) tissue samples exposed to a compound being evaluated. The amount of PDE activity can be determined by assaying for the amount of cyclic GMP in the extract of treated cells using RIA. When PDE activity is evaluated in this fashion, a combined cGMP hydrolytic activity is assayed. The test compound is then incubated with the tissue at a concentration of compound between about 200 μM to about 200 μM. About 24 to 48 hours thereafter, the culture media is removed from the tissue, and the cells are solubilized. The reaction is stopped by using 0.2N HCl/50% MeOH. A sample is removed for protein assay. Cyclic GMP is purified from the acid/alcohol extracts of cells using anion-exchange chromatography, such as a Dowex column. The cGMP is dried, acetylated according to published procedures, such as using acetic anhydride in triethylamine, (Steiner, A. L., Parker, C. W., Kipnis, D. M., *J. Biol. Chem.*, 247(4):1106–13, 1971, which is incorporated herein by reference). The acetylated cGMP is quantitated using radioimmunoassay procedures (Harper, J., Brooker, G., *Advances in Nucleotide Research*, 10: 1–33, 1979, which is incorporated herein by reference). Iodinated ligands (tyrosine methyl ester) of derivatized cyclic GMP are incubated with standards or unknowns in the presence of antisera and appropriate buffers. Antiserum may be produced using cyclic nucleotide-haptene directed techniques. The antiserum is from sheep injected with succinyl-cGMP-albumin conjugates and diluted 1/20,000. Dose-interpolation and error analysis from standard curves are applied as described previously (Seibert, A. F., Thompson, W. J., Taylor, A., Wilbourn, W. H., Barnard, J. and Haynes, J., *J. Applied Physiol.*, 72:389–395, 1992, which is incorporated herein by reference).

In addition, the tissue may be acidified, frozen (−70° C.) and also analyzed for cGMP and cAMP.

More specifically as to tissue testing, the PDE inhibitory activity effect of a compound can also be determined from tissue biopsies obtained from humans or tissues from animals exposed to the test compound. A sample of tissue is homogenized in 500 μl of 6% trichloroacetic acid ("TCA"). A known amount of the homogenate is removed for protein analysis. The remaining homogenate is allowed to sit on ice for 20 minutes to allow for the protein to precipitate. Next, the homogenate is centrifuged for 30 minutes at 15,000 g at 4° C. The supernatant is recovered, and the pellet recovered. The supernatant is washed four times with five volumes of water saturated diethyl ether. The upper ether layer is discarded between each wash. The aqueous ether extract is dried in a speed vac. Once dried, the sample can be frozen for future use, or used immediately. The dried extract is dissolved in 500 μl of assay buffer. The amount of PDE inhibition is determined by assaying for the amount of cyclic nucleotides using RIA procedures as described above.

In addition to compounds disclosed herein, other compounds that inhibit both PDE2 and PDE5 include compounds disclosed in U.S. Pat. Nos. 5,401,774 (e.g., exisulind), 6,063,818, 5,998,477, and 5,965,619. These patents are incorporated herein by reference.

When referring to an "a physiologically effective amount of an inhibitor of PDE2 and PDE5" we mean not only a single compound that inhibits those enzymes but a combination of several compounds, each of which can inhibit one or both of those enzymes. Single compounds that inhibit both enzymes are preferred.

When referring to an "inhibitor [that] does not substantially inhibit COX I or COX II," we mean that in the ordinary sense of the term. By way of example only, if the inhibitor has an IC$_{50}$ for either PDE2 or PDE5 that is at least half of the IC$_{50}$ of COXI and/or COXII, a drug achieving the PDE IC$_{50}$ in the blood could be said not to substantially inhibit the COX enzymes. Preferably, the IC$_{50}$ for the COX enzymes is in the order of 10 fold or more higher than the IC$_{50}$ for PDE2/PDE5. Preferably, the IC$_{50}$ for the COX enzymes is greater than about 40 μM.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to C$_1$ to C$_8$ alkyl groups.

The term "hydroxy-substituted lower alkyl" refers to lower alkyl groups that are substituted with at least one hydroxy group, preferably no more than three hydroxy groups.

The term "—SO$_2$(lower alkyl)" refers to a sulfonyl group that is substituted with a lower alkyl group.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example.

Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enaniomers may be synthesized from chiral starting materials, or the racemates can be resolved by conventional procedures that are well known in the art of chemistry such as chiral chromatography, fractional cyrstallization of diastereomeric salts and the like.

Compounds of Formula I also can exist as geometrical isomers (Z and E); the Z isomer is preferred.

Compounds of this invention may be formulated into pharmaceutical compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The compounds of this invention can be formulated with pharmaceutically acceptable carriers into unit dosage forms in a conventional manner so that the patient in need of therapy for type I diabetes can periodically (e.g., once or more per day) take a compound according to the methods of this invention. The exact initial dose of the compounds of this invention can be determined with reasonable experimentation. The initial dosage calculation would also take into consideration several factors, such as the formulation and mode of administration, e.g. oral or intravenous, of the particular compound. A total daily oral dosage of about 50 mg–2.0 gr of such compounds would achieve a desired systemic circulatory concentration. As discussed below, an oral dose of about 800 mg/day has been found appropriate in mammals.

As explained below, PDE2/5 inhibitors within this invention cause apoptosis in the infiltrating, activated macrophages that are associated with damage to pancreatic β-islet cells. Because the diabetic patient continually produces activated macrophages, PDE2/5 inhibitors of this invention should be administered chronically, i.e., for at least two weeks at a time. hi this manner, as any activated macrophages arise from monocytes, the drug in the patient's system can cause the macrophages to apoptose. In our hands, PDE2/5 inhibitors do cause monocytes to apoptose, given that animals exposed to such inhibitors chronically have normal monocyte blood counts.

The pharmaceutical compositions of this invention are preferably packaged in a container (e.g., a box or bottle, or both) with suitable printed material (e.g., a package insert) containing indications and directions for use in the treatment of type I diabetes, etc.

There are several general schemes for producing compounds of Formula I useful in this invention. One general scheme (which has several sub-variations) involves the case where both $R_3$ and $R_4$ are both hydrogen. This first scheme is described immediately below in Scheme I. The other general scheme (which also has several sub-variations) involves the case where at least one of $R_3$ and $R_4$ is a moiety other than hydrogen but within the scope of Formula I above. This second scheme is described below as "Scheme II."

The general scheme for preparing compounds where both $R_3$ and $R_4$ are both hydrogen is illustrated in Scheme I, which is described in part in U.S. Pat. No. 3,312,730, which is incorporated herein by reference. In Scheme I, $R_1$ is as defined in Formula I above. However, in Scheme I, that substituent can also be a reactive moiety (e.g. a nitro group) that later can be reacted to make a large number of other substituted indenes from the nitro-substituted indenes.

Scheme I
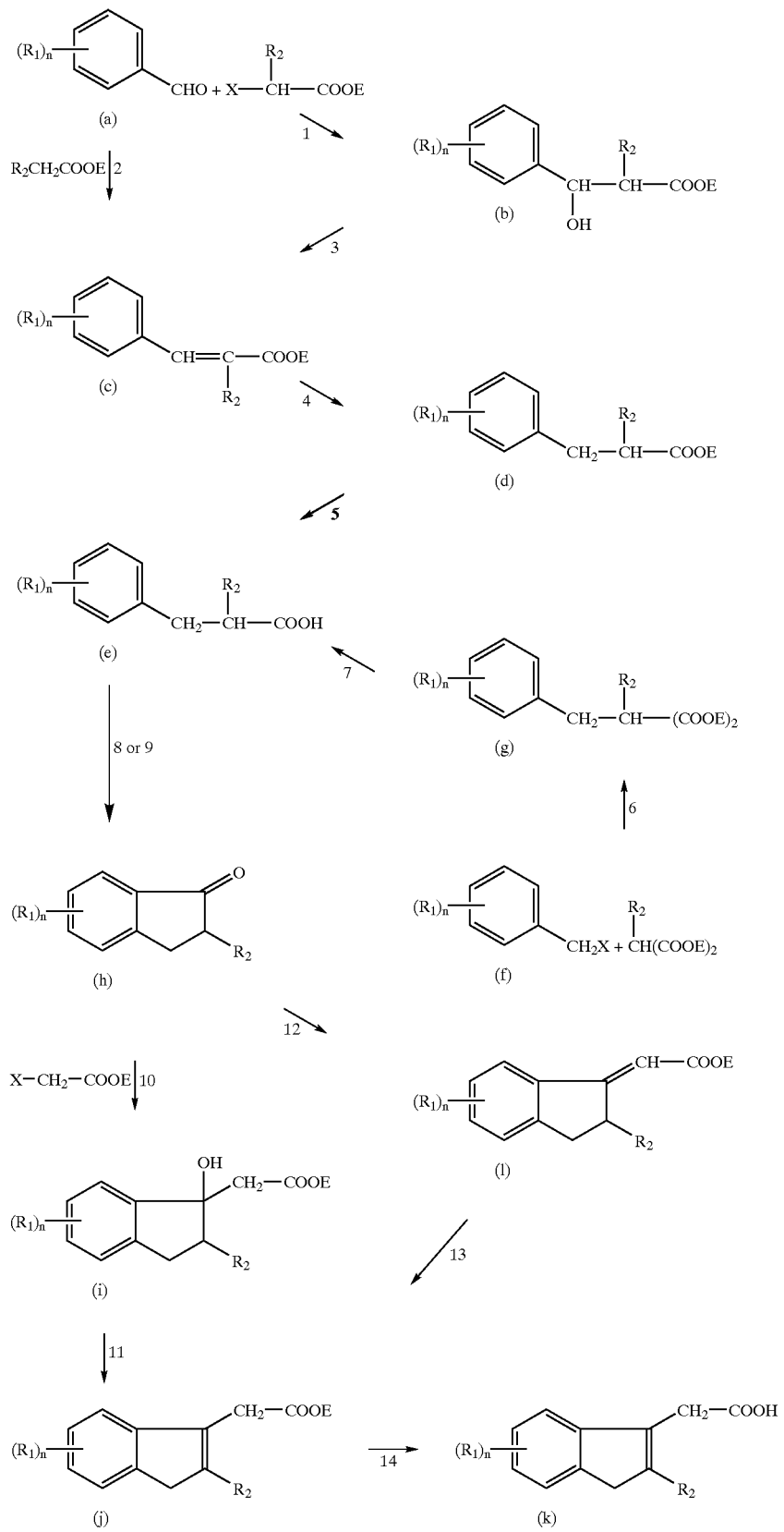

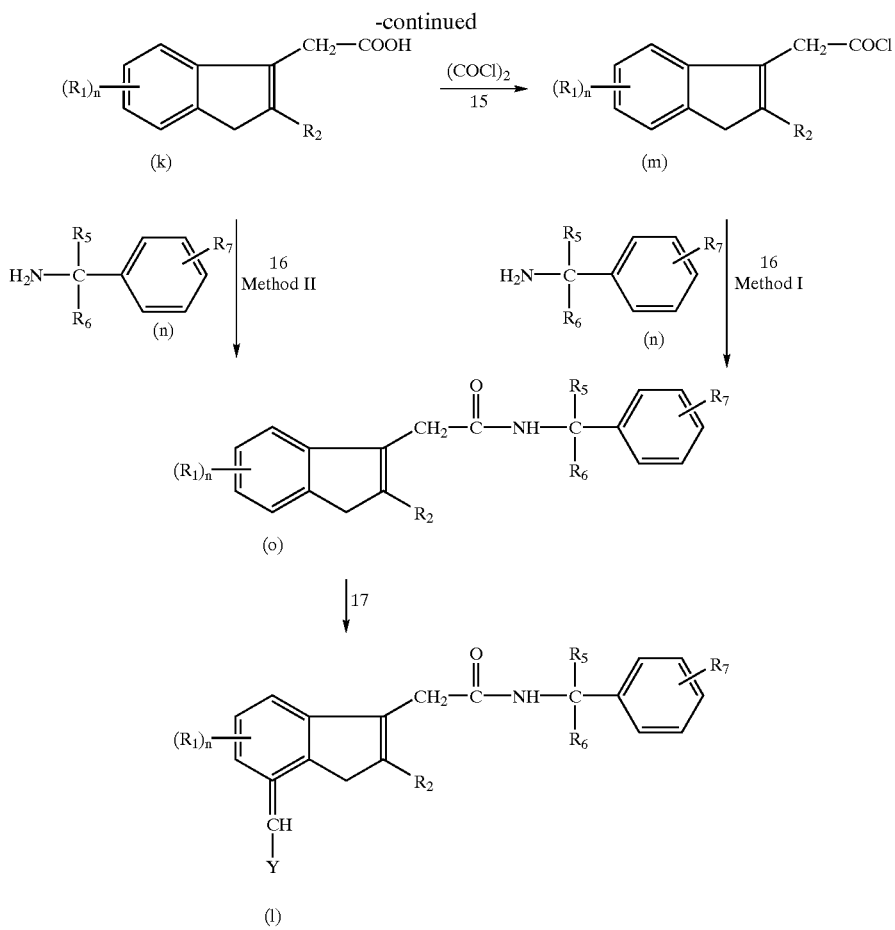

In Scheme I, several sub-variations can be used. In one sub-variation, a substituted benzaldehyde (a) may be condensed with a substituted acetic ester in a Knoevenagel reaction (see reaction 2) or with an a-halogeno propionic ester in a Reformatsky Reaction (see reactions 1 and 3). The resulting unsaturated ester (c) is hydrogenated and hydrolyzed to give a substituted benzyl propionic acid (e) (see reactions 4 and 5). Alternatively, a substituted malonic ester in a typical malonic ester synthesis (see reactions 6 and 7) and hydrolysis decarboxylation of the resulting substituted ester (g) yields the benzyl propionic acid (e) directly. This latter method is especially preferable for nitro and alkylthio substituents on the benzene ring.

The next step is the ring closure of the β-aryl proponic acid (e) to form an indanone (h) which may be carried out by a Friedel-Crafts Reaction using a Lewis acid catalyst (Cf. Organic Reactions, Vol. 2, p. 130) or by heating with polyphosphoric acid (see reactions 8 and 9, respectively). The indanone (h) may be condensed with an a-halo ester in the Reformatsky Reaction to introduce the aliphatic acid side chain by replacing the carboxyl group (see reaction 10). Alternately, this introduction can be carried out by the use of a Wittig Reaction in which the reagent is a α-triphenylphosphinyl ester, a reagent that replaces the carbonyl with a double bond to the carbon (see reaction 12). This product (1) is then immediately rearranged into the indene (j)(see reaction 13). If the Reformatsky Reaction route is used, the intermediate 3-hydroxy-3-aliphatic acid derivative i must be dehydrated to the indene (j) (see reaction 11).

The indenylacetic acid (k) in THF then is allowed to react with oxalyl or thionyl chloride or similar reagent to produce the acid chloride (m) (see reaction 15), whereupon the solvent is evaporated. There are two methods to carry out reaction 16, which is the addition of the benzylamine side chain (n).

Method (I)

In the first method, the benzylamine (n) is added slowly at room temperature to a solution of 5-fluoro-2-methyl-3-indenylacetyl chloride in $CH_2Cl_2$. The reaction mixture is refluxed overnight, and extracted with aqueous HCl (10%), water, and aqueous $NaHCO_3$ (5%). The organic phase is dried ($Na_2SO_4$) and is evaporated to give the amide compound (o).

Method (II)

In the second method, the indenylacetic acid (k) in DMA is allowed to react with a carbodiimide (e.g. N-(3-dimethylaminopropyl)-N'-ethylcarbodiimide hydrochloride) and benzylamine at room temperature for two days. The reaction mixture is added dropwise to stirred ice water. A yellow precipitate is filtered off, is washed with water, and is dried in vacuo. Recrystallization gives the amide compound (o).

Compounds of the type a' (Scheme III), o (Scheme I), t (Scheme II), y (Scheme IIB) may all be used in the condensation reaction shown in Scheme III.

Substituents

X=halogen, usually Cl or Br.

E=methyl, ethyl or benzyl, or lower acyl.

$R_1$, $R_2$, $R_6$, $R_5$, and $R_7$=as defined in Formula I.

Y, n and m=as defined in Formula I.

Reagents and general conditions for Scheme I (numbers refer to the numbered reactions):

(1) Zn dust in anhydrous inert solvent such as benzene and ether.
(2) $KHSO_4$ or p-toluene sulfonic acid.
(3) $NaOC_2H_5$ in anhydrous ethanol at room temperature.
(4) $H_2$ palladium on charcoal, 40 p.s.i. room temperature.
(5) NaOH in aqueous alcohol at 20–100°.
(6) $NaOC_2H_5$ or any other strong base such as NaH or K-t-butoxide.
(7) Acid.
(8) Friedel-Crafts Reaction using a Lewis Acid catalyst Cf. Organic Reactions, Vol. II, p. 130.
(9) Heat with polyphosphoric acid.
(10) Reformatsky Reaction: Zn in inert solvent, heat.
(11) p-Toluene sulfonic acid and $CaCl_2$ or $I_2$ at 200°
(12) Wittig Reaction using $(C_6H_5)_3$ P=C—COOE 20–80° in ether or benzene
(13) (a) $NBS/CCl_4$/benzoyl peroxide
    (b) $PtO_2/H_2$ (1 atm.)/acetic acid
(14) (a) NaOH
    (b) HCl
(15) Oxalyl or thionyl chloride in $CH_2Cl_2$ or THF
(16) Method I: 2 equivalents of $NH_2$—$C(R_5R_6)$—Ph—$(R_7)_m$
Method II: carbodiimide in THF
(17) $1N\ NaOCH_3$ in MeOH under reflux conditions Indanones within the scope of compound (h) in Scheme I are known in the literature and are thus readily available as intermediates for the remainder of the synthesis so that reactions 1–7 can be conveniently avoided. Among such known indanones are:

5-methoxyindanone 6-methoxyindanone 5-methylindanone 5-methyl-6-methoxyindanone 5-methyl-7-chloroindanone 4-methoxy-7-chloroindanone 4-isopropyl-2,7-dimethylindanone 5,6,7-trichloroindanone 2-n-butylindanone 5-methylthioindanone Scheme II has two mutually exclusive sub-schemes: Scheme IIA and Scheme IIB. Scheme IIA is used when $R_3$ is hydroxy and $R_4$ is hydrogen or when the two substituents form an oxo group. When $R_3$ is lower alkyl amino, Scheme IIB is employed.

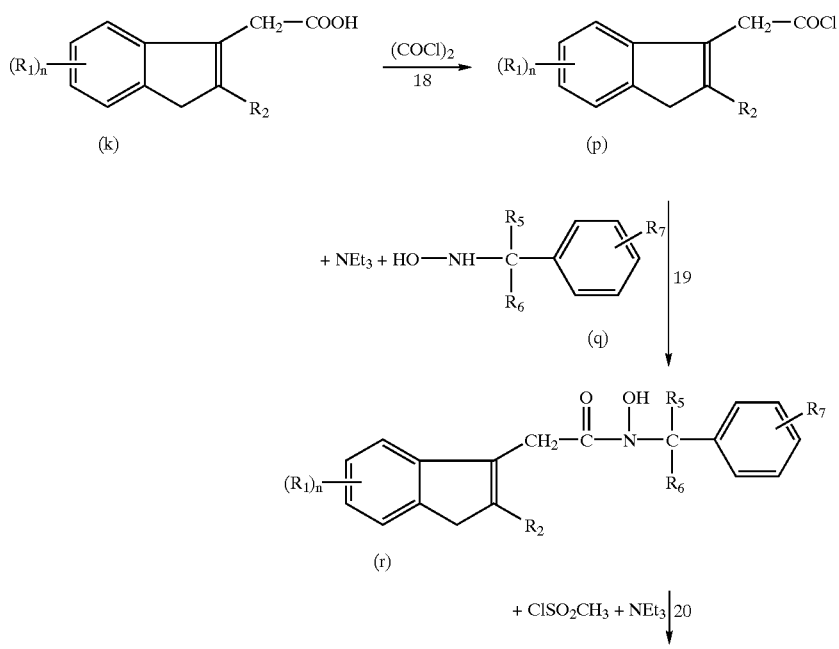

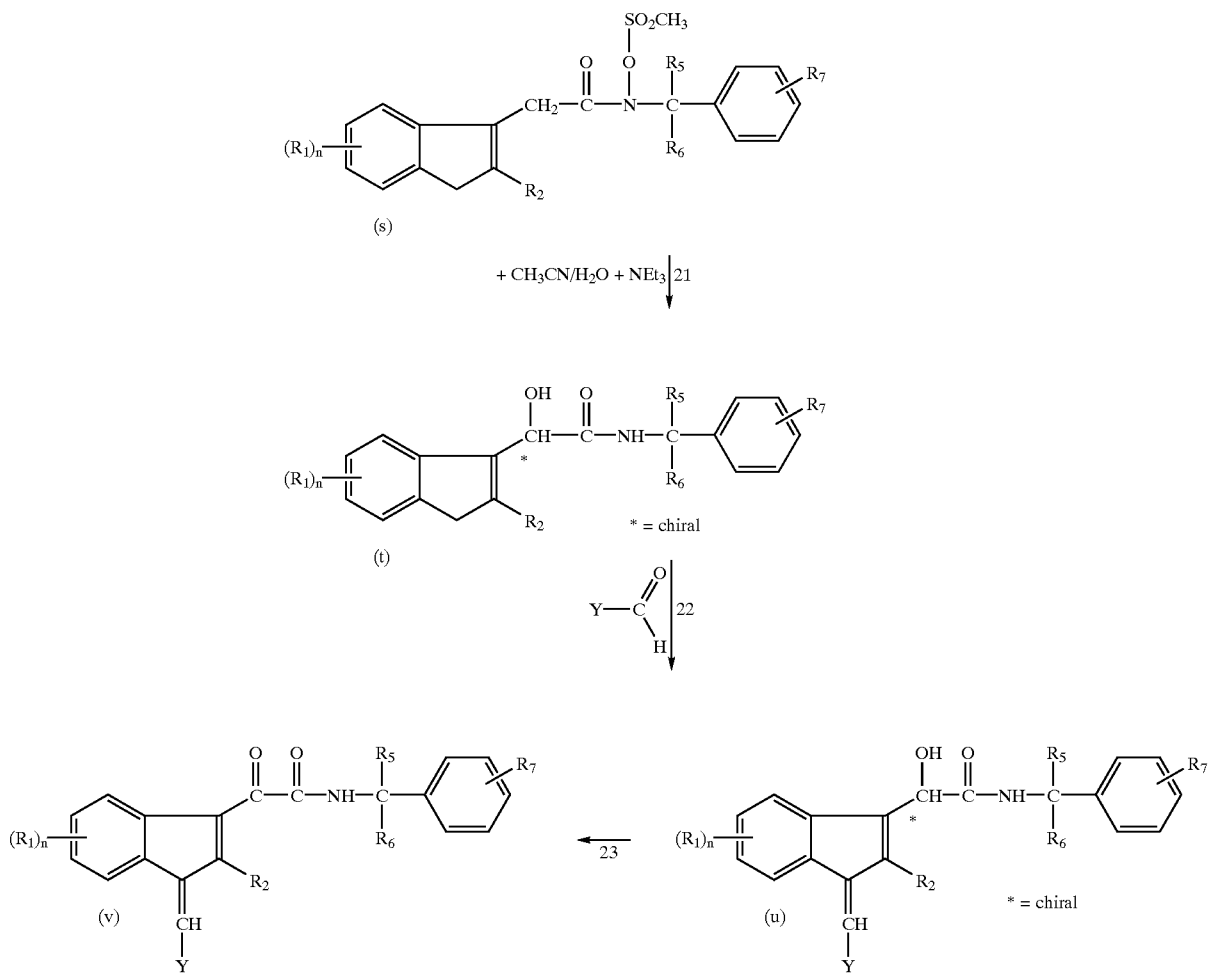

Similar to Scheme I, in Scheme IIA the indenylacetic acid (k) in THF is allowed to react with oxalyichloride under reflux conditions to produce the acid chloride (p) (see reaction 18), whereupon the solvent is evaporated. In reaction 19, a 0° C. mixture of a benzyl hydroxylamine hydrochloride (q) and $Et_3N$ is treated with a cold solution of the acid chloride in $CH_2Cl_2$ over a period of 45–60 minutes. The mixture is warmed to room temperature and stirred for one hour, and is treated with water. The resulting organic layer is washed with 1 N HCl and brine, is dried over magnesium sulfate and is evaporated. The crude product, a N-hydroxy-N-benzyl acetamide (r) is purified by crystallization or flash chromatography. This general procedure is taught by Hoffman et al., JOC 1992, 57, 5700–5707.

The next step is the preparation of the N-mesyloxy amide (s) in reaction 20, which is also taught by Hoffman et al., JOC 1992, 57, 5700–5707. Specifically, to a solution of the hydroxamic acid (r) in $CH_2Cl_2$ at 0° C. is added triethylamine. The mixture is stirred for 10–12 minutes, and methanesulfonyl chloride is added dropwise. The mixture is stirred at 0° C. for two hours, is allowed to warm to room temperature, and is stirred for another two hours. The organic layer is washed with water, 1 N HCl, and brine, and is dried over magnesium sulfate. After rotary evaporation, the product(s) is usually purified by crystallization or flash chromatography.

The preparation of the N-benzyl-α-(hydroxy) amide (t) in reaction 21, is also taught by Hoffman et al., JOC 1992, 57, 5700–5707 and Hoffman et al., JOC 1995, 60, 4121–4125. Specifically, to a solution of the N-(mesyloxy) amide (s) in $CH_3CN/H_2O$ is added triethylamine in $CH_3CN$ over a period of 6–12 hours. The mixture is stirred overnight. The solvent is removed, and the residue is dissolved in ethyl acetate. The solution is washed with water, 1 N HCl, and brine, and is dried over magnesium sulfate. After rotary evaporation, the product (t) is usually purified by recrystallization.

Reaction 22 in Scheme IIA involves a condensation with certain aldehydes, which is described in Scheme III below, a scheme that is common to products made in accordance with Schemes I, IIA and IIB.

The final reaction 23 in Scheme IIA is the preparation of the N-benzyl-α-ketoamide (v), which involves the oxidation of a secondary alcohol (u) to a ketone by e.g., a Pfitzner-Moffatt oxidation, which selectively oxidizes the alcohol without oxidizing the Y group. Compounds (u) and (v) may be derivatized to obtain compounds with $R_3$ and $R_4$ groups as set forth in Formula I.

Scheme IIB

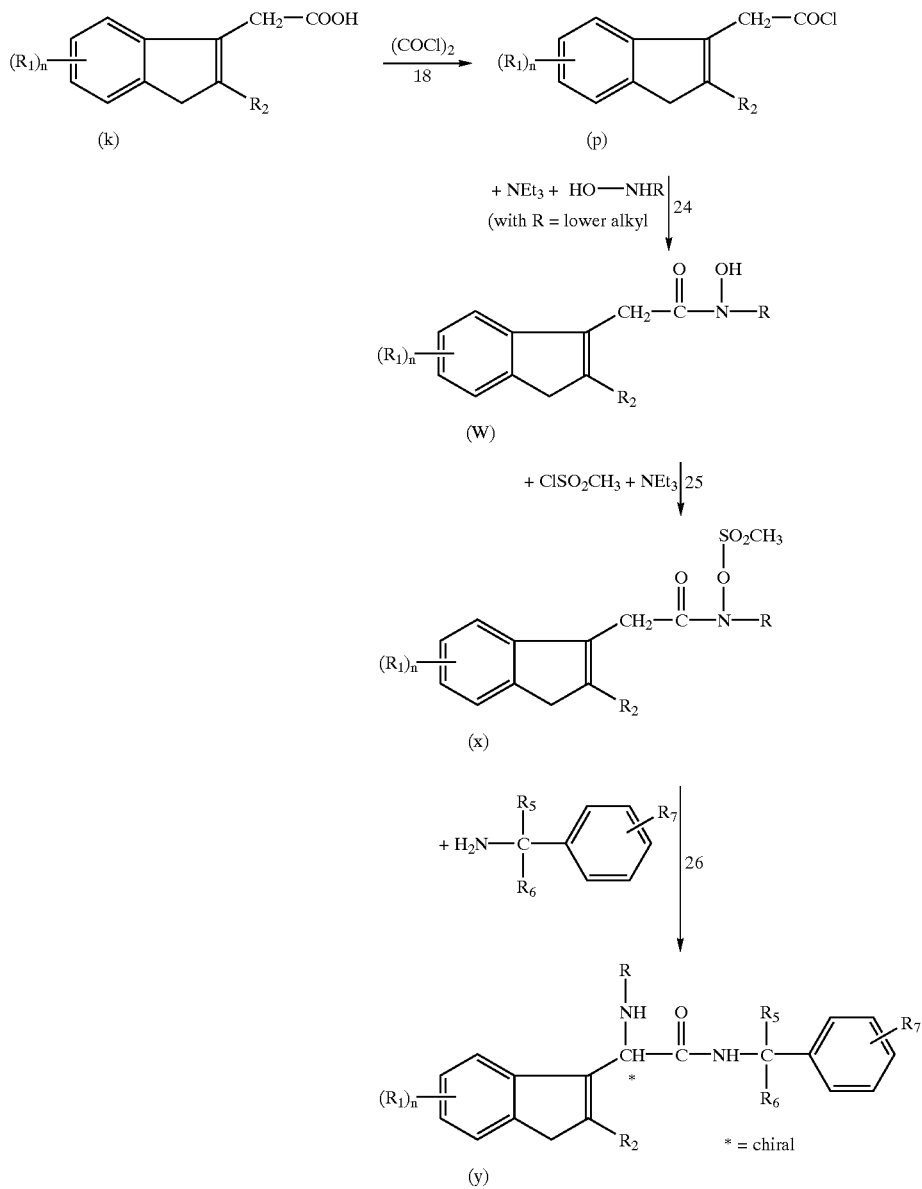

As explained above, Scheme II is employed when $R_3$ is lower alkyl amino. Similar to Scheme I, in Scheme IIB the indenylacetic acid (k) in THF is allowed to react with oxalylchloride under reflux conditions to produce the acid chloride (p) (see reaction 18), whereupon the solvent is evaporated. In reaction 24, a mixture of an alkyl hydroxylamine hydrochloride (i.e. HO—NHR where R is a lower alkyl, preferably isopropyl) and $Et_3N$ is treated at 0° C. with a cold solution of the acid chloride in $CH_2Cl_2$ over a period of 45–60 minutes. The mixture is warmed to room temperature and is stirred for one hour, and is diluted with water. The resulting organic layer is washed with 1 N HCl and brine, is dried over magnesium sulfate and is evaporated. The crude product, a N-hydroxy-N-alkyl acetamide (w) is purified by crystallization or flash chromatography. This general procedure is also taught by Hoffman et al., JOC 1992, 57, 5700–5707

The preparation of the N-mesyloxy amide (x) in reaction 25, which is also taught by Hoffman et al., JOC 1992, 57, 5700–5707. Specifically, a solution of the hydroxamic acid (w) in $CH_2Cl_2$ at 0° C. is treated with triethylamine, is stirred for 10–12 minutes, and is treated dropwise with methanesulfonyl chloride. The mixture is stirred at 0° C. for two hours, is allowed to warm to room temperature, and is stirred for another two hours. The resulting organic layer is washed with water, 1 N HCl, and brine, and is dried over magnesium sulfate. After rotary evaporation, the product (x) is usually purified by crystallization or flash chromatography.

The preparation of the N-benzyl indenyl-α-loweralkylainino-acetamide compound (y) in Scheme IIB as taught by Hoffman et al., JOC 1995, 60, 4121–25 and J. Am. Chem Soc. 1993, 115, 5031–34, involves the reaction of the N-mesyloxy amide (x), with a benzylamine in $CH_2Cl_2$ at 0° C. is added over a period of 30 minutes. The resulting solution is stirred at 0° C. for one hour and at room temperature overnight. The solvent is removed, and the residue is treated with 1 N NaOH. The extract with $CH_2Cl_2$ is washed with water and is dried over magnesium sulfate. After rotary evaporation, the product (y) is purified by flash chromatography or crystallization.

Scheme III

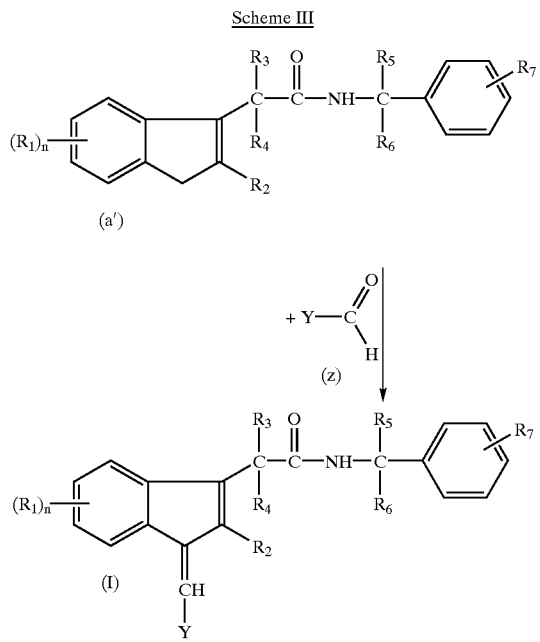

Scheme III involves the condensation of the heterocycloaldehydes (i.e., Y—CHO) with the indenyl amides to produce the final compounds of Formula I. This condensation is employed, for example, in reaction 17 in Scheme I above and in reaction 22 in Scheme IIA. It is also used to convert compound (y) in Scheme IIB to final compounds of Formula I.

In Scheme III, the amide (a') from the above schemes, an N-heterocycloaldehyde (z), and sodium methoxide (1 M in methanol) are stirred at 60° C. under nitrogen for 24 hours. After cooling, the reaction mixture is poured into ice water. A solid is filtered off, is washed with water, and is dried in vacuo. Recrystallization provides a compound of Formula I in Schemes I and IIB and the intermediate (u) in Scheme IIA.

As has been pointed out above, it is preferable in the preparation of many types of the compounds of this invention, to use a nitro substituent on the benzene ring of the indanone nucleus and convert it later to a desired substituent since by this route a great many substituents can be reached. This is done by reduction of the nitro to the amino group followed by use of the Sandmeyer reaction to introduce chlorine, bromine, cyano or xanthate in place of the amino. From the cyano derivatives, hydrolysis yields the carboxamide and carboxylic acid; other derivatives of the carboxy group such as the esters can then be prepared. The xanthates, by hydrolysis, yield the mercapto group that may be oxidized readily to the sulfonic acid or alkylated to an alkylthio group that can then be oxidized to alkylsulfonyl groups. These reactions may be carried out either before or after the introduction of the 1-substituent.

The foregoing may be better understood from the following examples that are presented for purposes of illustration and are not intended to limit the scope of the invention. As used in the following examples, the references to substituents such as $R_1$, $R_2$, etc., refer to the corresponding compounds and substituents in Formula I above.

EXAMPLE 1

(Z)-5-Fluoro-2-methyl-(4-pyridinylidene)-3-(N-benzyl)-indenylacetamide (A) p-Fluoro-α-methylcinnamic Acid p-Fluorobenzaldehyde (200 g, 1.61 mol), propionic anhydride (3.5 g, 2.42 mol) and sodium propionate (155 g, 1.61 mol) are mixed in a one liter three-necked flask which had been flushed with nitrogen. The flask is heated gradually in an oil-bath to 140° C. After 20 hours, the flask is cooled to 100° C. and poured into 8 l of water. The precipitate is dissolved by adding potassium hydroxide (302 g) in 2 l of water. The aqueous solution is extracted with ether, and the ether extracts are washed with potassium hydroxide solution. The combined aqueous layers are filtered, are acidified with concentrated HCl, and are filtered. The collected solid, p-fluoro-α-methylcinnamic acid, is washed with water, and is dried and used as obtained.

(B) p-Fluoro-α-methylhydrocinnamic Acid

To p-fluoro-α-methylcinnamic acid (177.9 g, 0.987 mol) in 3.6 l ethanol is added 11.0 g of 5% Pd/C. The mixture is reduced at room temperature under a hydrogen pressure of 40 p.s.i. When hydrogen uptake ceases, the catalyst is filtered off, and the solvent is evaporated in vacuo to give the product, p-fluoro-α-methylhydrocinnamic acid, which was used directly in the next step.

(C) 6-Fluoro-2-methylindanone

To 932 g polyphosphoric acid at 70° C. (steam bath) is added p-fluoro-α-methylhydrocinnamic acid (93.2 g, 0.5 mol) slowly with stirring. The temperature is gradually raised to 95° C., and the mixture is kept at this temperature for 1 hour. The mixture is allowed to cool and is added to 2 l. of water. The aqueous suspension is extracted with ether. The extract is washed twice with saturated sodium chloride solution, 5% $Na_2CO_3$ solution, and water, and is dried, and is concentrated on 200 g silica-gel; the slurry is added to a five pound silica-gel column packed with 5% ether-petroleum ether. The column is eluted with 5–10% ether-petroleum ether, to give 6-fluoro-2-methylindanone. Elution is followed by TLC.

(D) 5-Fluoro-2-methylindenyl-3-acetic Acid

A mixture of 6-fluoro-2-methylindanone (18.4 g, 0.112 mol), cyanoacetic acid (10.5 g, 0.123 mol), acetic acid (6.6 g), and ammonium acetate (1.7 g) in dry toluene (15.5 ml) is refluxed with stirring for 21 hours, as the liberated water is collected in a Dean Stark trap. The toluene is evaporated, and the residue is dissolved in 60 ml of hot ethanol and 14 ml of 2.2 N aqueous potassium hydroxide solution. 22 g of 85% KOH in 150 ml of water is added, and the mixture refluxed for 13 hours under nitrogen. The ethanol is removed under vacuum, and 500 ml water is added. The aqueous solution is extracted well with ether, and is then boiled with charcoal. The aqueous filtrate is acidified to pH 2 with 50% cold hydrochloric acid. The precipitate is dried and 5-fluoro-2-methylindenyl-3-acetic acid (M.P. 164–166° C.) is obtained.

(E) 5-Fluoro-2-methylindenyl-3-acetyl Chloride 5-fluoro-2-methylindenyl-3-acetic acid (70 mmol) in THF (70 ml) is allowed to react with oxalylchloride (2 M in $CH_2Cl_2$; 35 ml; 70 mmol) under reflux conditions (24 hours). The solvent is evaporated to yield the title compound, which is used as such in the next step.

(F) 5-Fluoro-2-methyl-3-(N-benzyl-indenylacetamide

Benzylamine (5 mmol) is added slowly at room temperature to a solution of 5-fluoro-2-methylindenyl-3-acetyl chloride (2.5 mmol.) in $CH_2Cl_2$ (10 ml). The reaction mixture is refluxed overnight, and is extracted with aqueous HCl (10%), water, and aqueous $NaHCO_3$ (5%). The organic phase is dried ($Na_2SO_4$) and is evaporated to give the title compound, which is recrystallized from $CH_2Cl_2$ to give the title compound as a white solid (m.p. 144° C.).

(G) (Z)-5-Fluoro-2-methyl-(4-pyridinhlidene)-3-(N-benzyl-indenylacetamide 5-fluoro-2-methyl-3-(N-benzyl)-indenylacetamide (3.38 mmol), 4-pyridinecarboxaldehyde (4 mmol), sodium methoxide (1M $NaOCH_3$ in methanol (30 ml)) are heated at 60° C. under nitrogen with stirring for 24 hours. After cooling, the reaction mixture is poured into ice water (200 ml). A solid is filtered off, washed with water, and dried in vacuo. Recrystallization from $CH_3CN$ gives the title compound (m.p. 202° C.) as a yellow solid ($R_1$=F, $R_2$=$CH_3$, $R_3$=H, $R_4$=H, $R_5$=H. $R_6$=H, $R_7$=H, n=1, m=1, Y=4-pyridinyl).

(H) (E)-5-Fluoro-2-methyl-(4-pyridinylidene)-3-(N-benzyl)-indenylacetamide

The mother liquor obtained from the $CH_3CN$ recrystallization of 1G is rich on the geometrical isomer of 1G. The E-isomer can be obtained pure by repeated recrystallizations from $CH_3CN$.

EXAMPLE 2

(Z)-5-Fluoro-2-methyl-(3-pyridinylidene)-3-(N-benzyl)-indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 3-pyridinecarboxaldehyde. Recrystallization from $CH_3CN$ gives the title compound (m.p. 175° C.)($R_1$=F, $R_2$=$CH_3$, $R_3$=H, $R_4$=H, $R_5$=H, $R_6$=H, $R_7$=H, n=1, m=1, Y=3-pyridinyl).

EXAMPLE 3

(Z)-5-Fluoro-2-methyl-(2-pyridinylidene)-3-(N-benzyl-indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 2-pyridinecarboxaldehyde. Recrystallization from ethylacetate gives the title compound (m.p. 218° C.)($R_1$=F, $R_2$=$CH_3$, $R_3$=H, $R_4$=H, $R_5$=H, $R_6$=H, $R_7$=H, n=1, m=1, Y=2-pyridinyl).

EXAMPLE 4

(Z)-5-Fluoro-2-methyl-(4-quinolipylidene)-3-(N-benzyl)-indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 4-quinolinecarboxaldehyde. Recrystallization from ethylacetate gives the title compound (m.p. 239° C.)($R_1$=F, $R_2$=$CH_3$, $R_3$=H, $R_4$=H, $R_5$=H, $R_6$=H, $R_7$=H, n=1, m=1, Y=2-pyridinyl).

EXAMPLE 5

(Z)-5-Fluoro-2-methyl-(4,6-dimethyl-2-pyridinylidene)-3-(N-benzyl)-indenylacetamide 5-Fluoro-2-methyl-3-(N-benzyl)-indenylacetamide from Example 1, part F is allowed to react with 4,6-dimethyl-2-pyridinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4,6-dimethyl-2-pyridinyl).

EXAMPLE 6

(Z)-5-Fluoro-2-methyl-(3-quinolinylidene)-3-(N-benzyl)-indenylacetamide

5-Fluoro-2-methyl-3-(N-benzyl)-indenylacetamide from Example 1, part F is allowed to react with 3-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=3-quinolinyl)

EXAMPLE 7

(Z)-5-Fluoro-2-methyl-(2-quinolinylidene-3-(N-benzyl)-indenylacetamide

5-Fluoro-2-methyl-3-(N-benzyl)-indenylacetamide from Example 1, part F is allowed to react with 2-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-quinolinyl).

EXAMPLE 8

(Z)-5-Fluoro-2-methyl-(Pyrazinylidene)-3-(N-benzyl)-indenylacetamide

5-Fluoro-2-methyl-3-(N-benzyl)-indenylacetamide from Example 1, part F is allowed to react with pyrazinealdehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m–1, Y=pyrazinyl).

EXAMPLE 9

(Z)-5-Fluoro-2-methyl-(3-pyridazinylidene)-3-(N-benzyl)-indenylacetamide

5-Fluoro-2-methyl-3-(N-benzyl)-indenylacetamide from Example 1, part F is allowed to react with pyridazine-3-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=3-pyridazinyl).

EXAMPLE 10

(Z)-5-Fluoro-2-methyl-(4-pyrimidinylidene)-3-(N-benzyl)-indenylacetamide

5-Fluoro-2-methyl-3-(N-benzyl)-indenylacetamide from Example 1, part F is allowed to react with pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4-pyrimidinyl).

EXAMPLE 11

(Z)-5-Fluoro-2-methyl-(2-methyl-4-pyrimidinylidene)-3-(N-benzyl)-indenylacetamide 5-Fluoro-2-methyl-3-(N-benzyl)-indenylacetamide from Example 1, part F is allowed to react with 2-methyl-pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-methyl-4-pyrimidinyl).

EXAMPLE 12

(Z)-5-Fluoro-2-methyl-(4-pyridazinylidene-3-(N-benzyl)-indenylacetamide

5-Fluoro-2-methyl-3-(N-benzyl)-indenylacetamide from Example 1, part F is allowed to react with pyridazine-4- aldehyde according to the procedure of Example 1, part G in order to obtain the title compound. Recrystallization gives the title compound ($R_1$=F, $R_2$=CH$_3$, $R_3$=H, $R_4$=H, $R_5$=H, $R_6$=H, $R_7$=H, n=1, m=1, Y=4-pyridazinyl).

EXAMPLE 13

(Z)-5-Fluoro-2-methyl-(1-methyl-3-indolylidene-3-(N-benzyl)-indenylacetamide

5-Fluoro-2-methyl-3-(N-benzyl)-indenylacetamide from Example 1, part F is allowed to react with 1-methylindole-3-carboxaldehyde according to the procedure of Example 1, part G in order to obtain the title compound. Recrystallization gives the title compound ($R_1$=F, $R_2$=CH$_3$, $R_3$=H, $R_4$=H, $R_5$=H, $R_6$=H, $R_7$=H, n=1, m=1, Y=1-methyl-3-indolyl).

EXAMPLE 14

(Z)-5-Fluoro-2-methyl-(1-acetyl-3-indolylidene)-3-(N-benzyl)-indenylacetamide

5-Fluoro-2-methyl-3-(N-benzyl)-indenylacetamide from Example 1, part F is allowed to react with 1-acetyl-3-indolecarboxaldehyde according to the procedure of Example 1, part G in order to obtain the title compound. Recrystallization gives the title compound ($R_1$=F, $R_2$=CH$_3$, $R_3$=H, $R_4$=H, $R_5$=H, $R_6$=H, $R_7$=H, n=1, m=1, Y=1-acetyl-3-indolyl).

EXAMPLE 15

(Z)-5-Fluoro-2-methyl-(4-pyrdinylidene)-3-(N-2-fluorobenzyl)-indenylacetamide (A) 5-Fluoro-2-methyl-3-(N-2-fluorobenzyl)-indenylacetamide This compound is obtained from 5-fluoro-2-methylindenyl-3-acetyl chloride (Example 1E) using the procedure of Example 1, Part F and replacing benzylamine with 2-fluorobenzylamine.

(B) (Z)-5-Fluoro-2-methyl-(4-pyridinylidene)-3-(N-2-fluorobenzy)-indenylacetamide 5-Fluoro-2-methyl-3-(N-2-fluorobenzyl)-indenylacetamide is allowed to react with 4-pryidinecarboxaldehyde according to the procedure of Example 1, part G in order to obtain the title compound. Recrystallization gives the title compound ($R_1$=F, $R_2$=CH$_3$, $R_3$=H, $R_4$=H, $R_5$=H, $R_6$=H, $R_7$=F, n=1, m=1, Y=4-pyridinyl).

EXAMPLE 16

(Z)-5-Fluoro-2-methyl-(3-pyridinylidene)-3-(N-2-fluorobenzyl)-indenylacetamide

5-Fluoro-2-methyl-3-(N-2-fluorobenzyl)-indenylacetamide from Example 15, part A is allowed to react with 3-pryidinecarboxaldehyde according to the procedure of Example 1, part G in order to obtain the title compound. Recrystallization gives the title compound ($R_1$=F, $R_2$=CH$_3$, $R_3$=H, $R_4$=H, $R_5$=H, $R_6$=H, $R_7$=F, n=1, m=1, Y=3-pyridinyl).

EXAMPLE 17

(Z)-5-Fluoro-2-methyl-(2-pyridinylidene)-3-(N-2-fluorobenzyl)-indenylacetamide

5-Fluoro-2-methyl-3-(N-2-fluorobenzyl)-indenylacetamide from Example 15, part A is allowed to react with 2-pyridinecarboxaldehyde according to the procedure of Example 1, part G in order to obtain the title compound. Recrystallization gives the title compound ($R_1$=F, $R_2$=CH$_3$, $R_3$=H, $R_4$=H, $R_5$=H, $R_6$=H, $R_7$=F, n=1, m=1, Y=2-pyridinyl).

EXAMPLE 18

(Z)-5-Fluoro-2-methyl-(4-quinolinlidene)-3-(N-2-fluorobenzyl)-indenylacetamide

5-Fluoro-2-methyl-3-(N-2-fluorobenzyl)-indenylacetamide from Example 15, part A is allowed to react with 4-quinolinecarboxaldehyde according to the procedure of Example 1, part G in order to obtain the title compound. Recrystallization gives the title compound ($R_1$=F, $R_2$=CH$_3$, $R_3$=H, $R_4$=H, $R_5$=H, $R_6$=H, $R_7$=H, n=1, m=1, Y=3-quinolinyl).

EXAMPLE 19

(Z)-5-Fluoro-2-methyl-(3-pyrazinylidene)-3-(N-2-fluorobenzyl)-indenylacetamide

5-Fluoro-2-methyl-3-(N-2-fluorobenzyl)-indenylacetamide from Example 15, part A is allowed to react with pyrazinealdehyde according to the procedure of Example 1, Part G in order to obtain the title compound. Recrystallization gives the title compound ($R_1$=F, $R_2$=CH$_3$, $R_3$=H, $R_4$=H, $R_5$=H, $R_6$=H, $R_7$=F, n=1, m=1, Y=3-pyrazinyl).

EXAMPLE 20

(Z)-5-Fluoro-2-methyl-(3-pyridazinylidene-3-(N-2-fluorobenzyl)-indenylacetamide

5-Fluoro-2-methyl-3-(N-2-fluorobenzyl)-indenylacetamide from Example 15, part A is allowed to react with 3-pryidaziine-3-aldehyde according to the procedure of Example 1, Part G in order to obtain the title compound. Recrystallization gives the title compound ($R_1$=F, $R_2$=CH$_3$, $R_3$=H, $R_4$=H, $R_5$=H, $R_6$=H, $R_7$=F, n=1, m=1, Y=3-pyridazinyl).

EXAMPLE 21

(Z)-5-Fluoro-2-methyl-(3-pyrimidinylidene)-3-(N-2-fluorobenzyl)-indenylacetamide 5-Fluoro-2-methyl-3-(N-2-fluorobenzyl)-indenylacetamide from Example 15, part A is allowed to react with pryimidine-4-aldehyde according to the procedure of Example 1, Part G in order to obtain the title compound. Recrystallization gives the title compound ($R_1$=F, $R_2$=CH$_3$, $R_3$=H, $R_4$=H, $R_5$=H, $R_6$=H, $R_7$=F, n=1, m=1, Y=3-pyrimidinyl).

EXAMPLE 22

(Z)-5-Fluoro-2-methyl-(4-pyridazylidene-3-(N-2-fluorobenzyl)-indenylacetamide

5-Fluoro-2-methyl-3-(N-2-fluorobenzyl)-indenylacetamide from Example 15, part A is allowed to react with pryidazine-4-aldehyde according to the procedure of Example 1, Part G in order to obtain the title compound. Recrystallization gives the title compound ($R_1$=F, $R_2$=CH$_3$, $R_3$=H, $R_4$=H, $R_5$=H, $R_6$=H, $R_7$=F, n=1, m=1, Y=4-pyridazinyl).

EXAMPLE 23

(Z)-5-Fluoro-2-methyl-(4-pyridinylidene)-3-(N-(S-α-hydroxymethyl)benzyl)-indenylacetamide (A) 5-Fluoro-2-methyl-3-(N-(S-α-hydroxylmethyl)benzyl)-indenylacetamide 5-Fluoro-2-methylindenyl-3-acetic acid (from Example 1D) (2.6 mmol) in DMA (2 ml) is allowed to react with n-(3-dimethylaminopropyl)-N'-ethylcarbodiimide hydrochloride (4 mmol) and S-2-amino-2-phenylethanol (3.5 mmol) at room temperature for two days. The reaction mixture is added dropwise to stirred ice water (50 ml). A white precipitate is filtered off, washed with water (5 ml), and dried in vacuo. Recrystallization from ethylacetate gives the desired compound.

(B) (Z)-5-Fluoro-2-methyl-(4-pyridinylidene)-3-(N-(S-α-hydroxymethyl)benzyl)-indenylacetamide 5-Fluoro-2-methyl-3-(N-(S-α-hydroxylmethyl)benzyl)-indenylacetamide from part A is allowed to react with 4-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridinyl).

EXAMPLE 24

(Z)-5-Fluoro-2-methyl-(3-pyridinylidene)-3-(N-(S-α-hydroxymethyl)benzyl)-indenylacetamide 5-Fluoro-2-methyl-3-(N-(S-α-hydroxymethyl)benzyl)-indenylacetamide from Example 23 part A is allowed to react with 3-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=3-pyridinyl).

EXAMPLE 25

(Z)-5-Fluoro-2-methyl-(2-pyridinylidene)-3-(N-(S-α-hydroxymethyl)benzyl-indenylacetamide 5-Fluoro-2-methyl-3-(N-(S-α-hydroxylmethyl)benzyl)-indenylacetamide from Example 23 part A is allowed to react with 2-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=2-pyridinyl).

EXAMPLE 26

(Z)-5-Fluoro-2-methyl-(4-quinolinylidene)-3-(N-(S-α-hydroxymethyl)benzyl)-indenylacetamide 5-Fluoro-2-methyl-3-(N-(S-α-hydroxylmethyl)benzyl)-indenylacetamide from Example 23 part A is allowed to react with 4-quinolinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-quinolinyl).

EXAMPLE 27

(Z)-5-Fluoro-2-methyl-(pyrazidinylidene)-3-(N-(S-α-hydroxymethyl)benzyl)-indenylacetamide 5-Fluoro-2-methyl-3-(N-(S-α-hydroxylmethyl)benzyl)-indenylacetamide from Example 23 part A is allowed to react with pryazidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=pyrazidinyl).

EXAMPLE 28

(Z)-5-Fluoro-2-methyl-(3-pyridazinylidene)-3-(N-S-α-hydroxymethyl)benzyl-indenylacetamide 5-Fluoro-2-methyl-3-(N-(S-α-hydroxymethyl)benzyl)-indenylacetamide from Example 23 part A is allowed to react with pryidazine-3-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=3-pyridazinyl).

EXAMPLE 29

(Z)-5-Fluoro-2-methyl-(4-pyrimidinylidene)-3-(N-(S-α-hydroxymethyl)benzyl-indenylacetamide 5-Fluoro-2-methyl-3-(N-(S-α-hydroxylmethyl)benzyl)-indenylacetamide from Example 23 part A is allowed to react with pryimidine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyrimidinyl).

EXAMPLE 30

(Z)-5-Fluoro-2-methyl-(4-pyridazinylidene)-3-(N-(S-α-hydroxymethyl)benzyl)-indenylacetamide 5-Fluoro-2-methyl-3-(N-(S-α-hydroxylmethyl)benzyl)-indenylacetamide from Example 23 part A is allowed to react with pryidazine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridazinyl).

EXAMPLE 31 rac-(Z)-5-Fluoro-2-methyl-(4-pyridinylidene)-3-(N-benzyl)indenyl-α-hydroxyacetamide (A) 5-Fluoro-2-methyl-3-(N-benzyl-N-hydroxy)-indenylacetamide To a mixture of N-benzylhydroxylamine hydrochoride (12 mmol) and $Et_3N$ (22 mmol) in $CH_2Cl_2$ (100 ml) at 0° C. is added a cold solution of 5-Fluoro-2-methylindenyl-3-acetyl chloride (Example 1, Step E) (10 mmol) in $CH_2Cl_2$ (75 ml) over a period of 45–60 minutes. The mixture is warmed to room temperature and is stirred for 1 hour. The mixture is diluted with water (100 ml), and the organic layer is washed with HCl (2×25 ml) and brine (2×100 ml), dried ($MgSO_4$) and evaporated. The crude product is purified with flash chromatography to give the title compound.

(B) 5-Fluoro-2-methyl-3-(N-benzyl-N-mesyloxy)-indenylacetamide

To a solution of 5-Fluoro-2-methyl-3-(N-benzyl-N-hydroxy)-indenylacetamide (5 mmol) in $CH_2Cl_2$ (25 ml) at 0° C. is added triethylamine (5 mmol). The mixture is stirred for 10 minutes, and methanesulfonyl chloride (5.5 mmol) is added dropwise. The solution is stirred at 0° C. for 2 hours, allowed to warm to room temperature, and stirred for another 2 hours. The organic layer is washed with water (2×20 ml), in HCl (15 ml), and brine (20 ml) and dried over MgSO$_4$. After rotary evaporation, the product is purified with flash chromatography to give the title compound.

(C) rac-5-Fluoro-2-methyl-3-(N-benzyl)-α-hydroxyindenylacetamide

To a solution of 5-Fluoro-2-methyl-3-(N-benzyl-N-mesyloxy)-indenylacetamide (2 mmol) in CH$_3$CN/H$_2$O (12 ml. each) is added triethylamine (2.1 mmol) in CH$_3$CN (24 ml) over a period of 6 hours. The mixture is stirred overnight. The solvent is removed, and the residue diluted with ethyl acetate (60 ml), washed with water (4×20 ml), in HCl (15 ml), and brine (20 ml) and dried over MgSO$_4$. After rotary evaporation, the product is purified by recrystallization to give the title compound.

(D) rac-(Z)-5-Fluoro-2-methyl-(4-pyridinylidene)-3-(N-benzyl)-indenyl-α-hydroxyacetamide is obtained from rac-5-Fluoro-2-methyl-3-(N-benzyl)-α-hydroxyindenylacetamide using the procedure of Example 1, Part G (R$_1$=F, R$_2$=CH$_3$, R$_3$=OH, R$_4$=H, R$_5$=H, R$_6$=H, R$_7$=H, n=1, m=1, Y=4-pyridinyl).

EXAMPLE 32

2-[(Z)-5-Fluoro-2-methyl-(4-pyridinylidene)-3-(N-benzyl)-indenyl]-oxyacetamide

For Pfitzner-Moffatt oxidation, a solution of rac-(Z)-5-Fluoro-2-methyl-(4-pyridinylidene)-3-(N-benzyl)-indenyl-α-hydroxyacetamide (1 mmol) in DMSO (5 ml) is treated with dicyclohexylcarbodiimide (3 mmol). The mixture is stirred overnight, and the solvent is evaporated. The crude product is purified by flash chromatography to give the title compound (R$_1$=F, R$_2$=CH$_3$, R$_3$ and R$_4$ together form C=O, R$_5$=H, R$_6$=H, R$_7$=H, n=1, m=1, and Y=4-pyridinyl).

EXAMPLE 33 rac-(Z)-5-Fluoro-2-methyl-(4-pyridinylidene)-3-(N-benzyl)-indenyl-α-(2-propylamino)-acetamide (A) 5-luoro-2-methyl-3-(N-2-propyl-N-hydroxy)-indenylacetamide is obtained from 5-fluoro-2-methylindenyl-3-acetyl chloride (Example 1, Step E) using the procedure of Example 31, Part A and replacing N-benzylhydroxylamine hydrochloride with N-2-propyl hydroxylamine hydrochloride.

(B) 5-Fluoro-2-methyl-3-(N-2-propyl-N-mesyloxy)-indenylacetamide is obtained according to the procedure of Example 31, Part B.

(C) rac-5-Fluoro-2-methyl-3-(N-benzyl)-α-(2-propylamino)-acetamide. To 5-fluoro-2-methyl-3-(N-2-propyl-N-mesyloxy)-indenylacetamide (2 mmol) in CH$_2$Cl$_2$ (25 ml) at 0° C. is added benzylamine (4.4 mmol) in CH$_2$Cl$_2$ (15 ml) over a period of 30 minutes. The resulting solution is stirred at 0° C. for 1 hour, and at room temperature overnight. The solvent is removed, and the residue is treated with 1 N NaOH, and is extracted with CH$_2$Cl$_2$ (100 ml). The extract is washed with water (2×10 ml), and is dried over MgSO$_4$. After rotary evaporation, the product is purified by flash chromatography.

(D) rac-(Z)-5-fluoro-2-methyl-(4-pyridinylidene)-3-(N-benzyl-indenyl-α-(2-propylamino)-acetamide is obtained from rac-5-fluoro-2-methyl-3-(N-benzyl)-α-(2-propylamino)-acetamide using the procedure of Example 1, Part G (R$_1$=F, R$_2$=CH$_3$, R$_3$=isopropylamino, R$_4$=H, R$_5$=H, R$_6$=H, R$_7$=H, n=1, m=1, Y=4-pyridinyl).

EXAMPLE 34

(Z)-6-Methoxy-2-methyl-(4-pyridinylidene)-3-(N-benzyl)-indenylacetamide (A) Ethyl-2-hydroxy-2-(p-methoxyphenyl)-1-methylpropionate In a 500 ml. 3-necked flask is placed 36.2 g. (0.55 mole) of zinc dust, a 250 ml. addition funnel is charged with a solution of 80 ml. anhydrous benzene, 20 ml. of anhydrous ether, 80 g. (0.58 mole) of p-anisaldehyde and 98 g. (0.55 mole) of ethyl-2-bromoproplonate. About 10 ml. of the solution is added to the zinc dust with vigorous stirring, and the mixture is warmed gently until an exothermic reaction commences. The remainder is added dropwise at such a rate that the reaction mixture continues to reflux smoothly (ca. 30–35 min.). After addition is completed the mixture is placed in a water bath and refluxed for 30 minutes. After cooling to 0°, 250 ml. of 10% sulfuric acid is added with vigorous stirring. The benzene layer is extracted twice with 50 ml. portions of 5% sulfuric acid and washed twice with 50 ml. portions of water. The combined aqueous acidic layers are extracted with 2×50 ml. ether. The combined etheral and benzene extracts are dried over sodium sulfate. Evaporation of solvent and fractionation of the residue through a 6" Vigreux column affords 89 g. (60%) of the product, ethyl-2-hydroxy-2-(p-methoxyphenyl)-1-methylpropionate, B.P. 165–160° (1.5 mm.).

(B) 6-Methoxy-2-methylindanone

By the method described in Vander Zanden, Rec. Trav. Chim., 68, 413 (1949), the compound from part A is converted to 6-methoxy-2-methylindanone.

Alternatively, the same compound can be obtained by adding α-methyl-β-(p-methoxylphenyl)propionic acid (15 g.) to 170 g. of polyphosphoric acid at 50° and heating the mixture at 83–90° for two hours. The syrup is poured into iced water. The mixture is stirred for one-half hour, and is extracted with ether (3×). The etheral solution is washed with water (2×) and 5% NaHCO$_3$ (5×) until all acidic material has been removed, and is dried over sodium sulfate. Evaporation of the solution gives 9.1 g. of the indanone as a pale yellow oil.

(C) (Z)-6-Methoxy-2-methyl-(4-pyridinylidene)-3-(N-benzyl)-indenylacetamide

In accordance with the procedures described in Example 1, parts D–G, this compound is obtained substituting 6-methoxy-2-methylindanone for 6-fluoro-2-methylindanone in part D of Example 1.

EXAMPLE 35

(Z)-5-Methoxy-2-methyl-(4-pyridinylidene)-3-(N-benzyl)-indenylacetamide (A) Ethyl 5-Methoxy-2-methyl-3-indenyl Acetate A solution of 13.4 g of 6-methoxy-2-methylindanone and 21 g. of ethyl bromoacetate in 45 ml. benzene is added over a period of five minutes to 21 g. of zinc amalgam (prepared according to Org. Syn. Coll. Vol. 3) in 110 ml. benzene and 40 ml. dry ether. A few crystals of iodine are added to start the reaction, and the reaction mixture is maintained at reflux temperature (ca. 65°) with external heating. At three-hour intervals, two batches of 10 g. zinc amalgam and 10 g. bromoester are added and the mixture is then refluxed for 8 hours. After addition of 30 ml. of ethanol and 150 ml. of acetic acid, the mixture is poured into 700 ml. of 50% aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° (bath temperature)(1–2 mm.) gives crude ethyl-(1-hydroxy-2-methyl-6-methoxy-indenyl) acetate (ca. 18 g.).

A mixture of the above crude hydroxyester, 20 g. of p-toluenesulfonic acid monohydrate and 20 g. of anhydrous calcium chloride in 250 ml. toluene is refluxed overnight.

The solution is filtered, and the solid residue is washed with toluene. The combined toluene solution is washed with water, sodium bicarbonate, water and then dried over sodium sulfate. After evaporation, the crude ethyl 5-methoxy-2-methyl-3-indenyl acetate is chromatographed on acid-washed alumina, and the product is eluted with petroleum ether-ether (v./v. 50–100%) as a yellow oil (11.8 g., 70%).

(B) (Z)-5-Methoxy-2-methyl-(4-pyridinylidene)-3-(N-benzyl)-indenylacetamide

In accordance with the procedures described in Example 1, parts E–G, this compound is obtained substituting ethyl-5-methoxy-2-methyl-3-indenyl acetate for 5-fluoro-2-methylindenyl-3-acetic acid in Example 1, part E.

EXAMPLE 36

(Z)-α-5-Methoxy-2-methyl-(4-pyridinylidene)-3-(N-benzyl)-indenylpropionamide (A) α-(5-Methoxy-2-methyl-3-indenyl)propionic Acid The procedure of Example 35, part (A) is followed using ethyl α-bromopropionate in equivalent quantities in place of ethyl bromoacetate used therein. There is obtained ethyl α-(1-hydroxy-6-methoxy-2-methyl-1-indanyl)propionate, which is dehydrated to ethyl α-(5-methoxy-2-methyl-3-indenyl)propionate in the same manner.

The above ester is saponified to give α-(5-methoxy-2-methyl-3-indenyl)propionic acid.

(B) (Z)-α-5-Methoxy-2-methyl-(4-pyridinyl)-3-(N-benzyl)-α-methylindenylpropionamide In accordance with the procedures described in Example 1, parts E–G, this compound is obtained substituting α-5-methoxy-2-methyl-3-indenyl)propionic acid for 5-Fluoro-2-methylindenyl-3-acetic acid in Example 1, part E.

EXAMPLE 37

(Z) α-Fluoro-5-Methoxy-2-methyl-(4-pyridinylidene)-3-(N-benzyl)indenylacetamide (A) Methyl-5-methoxy-2-methyl-3-indenyl-α-fluoro Acetate A mixture of potassium fluoride (0.1 mole) and methyl-5-methoxy-2-methyl-3-indenyl-α-tosyloxy acetate (0.05 mole) in 200 ml. dimethylformamide is heated under nitrogen at the reflux temperature for 2–4 hours. The reaction mixture is cooled, poured into iced water and then extracted with ether. The ethereal solution is washed with water, sodium bicarbonate and dried over sodium sulfate. Evaporation of the solvent and chromatography of the residue on an acid-washed alumina column (300 g.) using ether-petroleum ether (v./v. 20–50%) as eluent give the product, methyl-5-methoxy-2-methyl-3-indenyl-α-fluoroacetate.

(B) (Z) α-Fluoro-5-methoxy-2-methyl-(4-pyridinylidene)-3-(N-benzyl)indenylacetamide In accordance with the procedures described in Example 1, parts E–G, this compound is obtained substituting methyl-5-methoxy-2-methyl-3-indenyl-α-fluoroacetate for 5-Fluoro-2-methylindenyl-3-acetic acid in Example 1, part E.

For the introduction of the =CH—Y part in Scheme III, any of the appropriate heterocyclic aldehydes may be used either directly in the base-catalyzed condensation or in a Wittig reaction in an alternative route. The aldehydes that may be used are listed in Table 1 below:

TABLE 1 pyrrol-2-aldehyde*
pyrimidine-2-aldehyde
6-methylpyridine-2-aldehyde*
1-methylbenzimidazole-2-aldehyde
isoquinoline-4-aldehyde
4-pyridinecarboxaldehyde*
3-pyridinecarboxaldehyde*
2-pyridinecarboxaldehyde*
4,6-dimethyl-2-pyridinecarboxaldehyde*
4-methyl-pyridinecarboxaldehyde*
4-quinolinecarboxaldehyde*
3-quinolinecarboxaldehyde*
2-quinolinecarboxaldehyde*
2-chloro-3-quinolinecarboxaldehyde*
pyrazinealdehyde
(Prepared as described by Rutner et al., JOC 1963, 28, 1898–99)
pyridazine-3-aldehyde
(Prepared as described by Heinisch et al., Monatshefte Fuer Chemie 108, 213–224, 1977)
pyrimidine-4-aldehyde
(Prepared as described by Bredereck et al., Chem. Ber. 1964, 97, 3407–17)
2-methyl-pyrimidine-4-aldehyde
(Prepared as described by Bredereck et al., Chem. Ber. 1964 97, 3407–17)
pyridazine-4-aldehyde
(Prepared as described by Heinisch et al., Monatshefte Fuer Chemie 104, 1372–1382 (1973))
1-methylindole-3-carboxaldehyde*
1-acetyl-3-indolecarboxaldehyde*

*Available from Aldrich

The aldehydes above can be used in the reaction schemes above in combination with various appropriate amines to produce compounds with the scope of this invention. Examples of appropriate amines are those listed in Table 2 below:

TABLE 2 benzylamine
2,4-dimethoxybenzylamine
2-methoxybenzylamine
2-fluorobenzylamine
4-dimethylaminobenzylamine
4-sulfonaminobenzylamine
1-phenylethylamine (R-enantiomer)
2-amino-2-phenylethanol (S-enantiomer)
2-phenylglycinonitrile (S-enantiomer)

EXAMPLE 38

(Z)-5-Fluoro-2-methyl-(4-pyridylidene)-3-(N-benzyl)indenylacetamide Hydrochloride (Z)-5-Fluoro-2-methyl-(4-pyridylidene)-3-(N-benzyl) indenylacetamide (1396 g; MW 384.45; 3.63 mol) from Example 1 is dissolved at 45° C. in ethanol (28 L). Aqueous HCl (12 M; 363 mL) is added stepwise. The reaction mixture is heated under reflux for 1 hour, is allowed to cool to room temperature, then stored at −10° C. for 3 hours. The resulting solid is filtered off, is washed with ether (2×1.5 L) and is air-dried overnight. Drying under vacuum at 70° C. for 3 days gives (Z)-5-fluoro-2-methyl-(4-pyridylidene)-3-(N-benzyl)indenylacetamide hydrochloride with a melting point of 207–209° C. ($R_1$=F, $R_2$=$CH_3$, $R_3$=H, $R_4$=H, $R_5$=H, $R_6$=H, $R_7$=H, n=1, m=1, Y=4-pyridinyl·hydrochloride). Yield: 1481 g (97%; 3.51 mol); MW: 420.91 g/mol.

$^1$H-NMR (DMSO-$d_6$): 2.18 (s, 3, =C—$CH_3$); 3.54 (s, 2, =$CH_2$CO); 4.28 (d, 2, N$CH_2$); 6.71 (m, 1, ar.); 7.17 (m, 8, ar.); 8.11 (d, 2, ar., AB system); 8.85 (m, 1, NH); 8.95 (d, 2, ar., AB system); IR (KBr): 3432 NH; 1635 C=O; 1598 C=C.

EXAMPLE 39

(Z)-5-Fluoro-2-methyl-(4-pyridylidene)-3-(N-benzyl)-indenylacetamide p-methylbenzenesulfonate (Z)-5-fluoro-2-methyl-(4-pyridylene)-3-(N-benzyl) indenylacetamide (MW=384.46 g/mol; 5.21 mmol; 2 g) from Example 1 is dissolved in ethanol (50 ml). Solid p-toluenesulfonic acid monohydrate (MW=190.22 g/mol; 5.21 mmol; 991 mg) is added to the stirred solution. The reaction mixture is stirred for 12 hours at room temperature. The ethanol is evaporated in aspirator vacuum. The residue is dried in high vacuum to yield (Z)-5-Fluoro-2-methyl-(4-pyridylidene)-3-(N-benzyl)-indenylacetamide p-methylbenzenesulfonate as an orange-red powder.

As to identifying structurally additional PDE2 and PDE5 inhibiting compounds besides those of Formula I that can be effective therapeutically for type I diabetes, one skilled in the art has a number of useful model compounds disclosed herein (as well as their analogs) that can be used as the bases for computer modeling of additional compounds having the same conformations but different chemically. For example, software such as that sold by Molecular Simulations Inc. release of WebLab® ViewerPro™ includes molecular visualization and chemical communication capabilities. Such software includes functionality, including 3D visualization of known active compounds to validate sketched or imported chemical structures for accuracy. In addition, the software allows structures to be superimposed based on user-defined features, and the user can measure distances, angles, or dihedrals.

In this situation, since the structures of active compounds are disclosed above, one can apply cluster analysis and 2D and 3D similarity search techniques with such software to identify potential new additional compounds that can then be screened and selected according to the selection criteria of this invention. These software methods rely upon the principle that compounds, which look alike or have similar properties, are more likely to have similar activity, which can be confirmed using the PDE selection criterion of this invention.

Likewise, when such additional compounds are computer-modeled, many such compounds and variants thereof can be synthesized using known combinatorial chemistry techniques that are commonly used by those of ordinary skill in the pharmaceutical industry. Examples of a few for-hire combinatorial chemistry services include those offered by New Chemical Entities, Inc. of Bothell, Wash., Protogene Laboratories, inc., of Palo Alto, Calif., Axys, Inc. of South San Francisco, Calif., Nanosyn, Inc. of Tucson, Ariz., Trega, Inc. of San Diego, Calif., and RBI, Inc. of Natick, Mass. There are a number of other for-hire companies. A number of large pharmaceutical companies have similar, if not superior, in-house capabilities. In short, one skilled in the art can readily produce many compounds for screening from which to select promising compounds for treatment of neoplasia having the attributes of compounds disclosed herein.

To further assist in identifying compounds that can be screened and then selected using the criterion of this invention, knowing the binding of selected compounds to PDE5 and PDE2 protein is of interest. By the procedures discussed below, it is believed that preferable, desirable compounds meeting the selection criteria of this invention bind to the cGMP catalytic regions of PDE2 and PDE5.

To establish this, a PDE5 sequence that does not include the catalytic domain can be used. One way to produce such a sequence is to express that sequence as a fusion protein, preferably with glutiathione S-transferase ("GST"), for reasons that will become apparent.

RT-PCR method is used to obtain the cGB domain of PDE5 with forward and reverse primers designed from bovine PDE5A cDNA sequence (McAllister-Lucas L. M. et al, *J. Biol. Chem.* 268, 22863–22873, 1993) and the selection among PDE 1–10 families. 5'-3', Inc. kits for total RNA followed by oligo (dT) column purification of mRNA are used with HT-29 cells. Forward primer (GAA-TTC-TGT-TAG-AAA-AGC-CAC-CAG-AGA-AAT-G, 203–227) and reverse primer (CTC-GAG-CTC-TCT-TGT-TTC-TTC-CTC-TGC-TG, 1664–1686) are used to synthesize the 1484 bp fragment coding for the phosphorylation site and both low and high affinity cGMP binding sites of human PDE5A (203–1686 bp, cGB-pDE5). The synthesized cGB-pDE5 nucleotide fragment codes for 494 amino acids with 97% similarity to bovine PDE5A. It is then cloned into pGEX-5X-3 glutathione-S-ransferase (GST) fusion vector (Pharmacia Biotech )with tac promoter, and EcoRI and XhoI cut sites. The fusion vector is then transfected into *E. Coli* BL21 (DE3) bacteria (Invitrogen). The transfected BL21 bacteria is grown to log phase, and then IPTG is added as an inducer. The induction is carried at 20° C. for 24 hrs. The bacteria are harvested and lysed. The soluble cell lysate is incubated with GSH conjugated Sepharose 4B (GSH-Sepharose 4B). The GST-cGB-pDE5 fusion protein can bind to the GSH-Sepharose beads, and the other proteins are washed off from beads with excessive cold PBS.

The expressed GST-cGB-pDE5 fusion protein is displayed on 7.5% SDS-PAGE gel as an 85 Kd protein. It is characterized by its cGMP binding and phosphorylation by protein kinases G and A. It displays two cGMP binding sites, and the $K_d$ is 1.6±0.2 $\mu M$, which is close to $K_d$=1.3 $\mu M$ of the native bovine PDE5. The GST-cGB-PDE5 on GSH-conjugated sepharose beads can be phosphorylated in vitro by cGMP-dependent protein kinase and cAMP-dependent protein kinase A. The $K_m$ of GST-cGB-pDE5 phosphorylation by PKG is 2.7 $\mu M$ and Vmax is 2.8 $\mu M$, while the $K_m$ of BPDEtide phosphorylation is 68 $\mu M$. The phosphorylation by PKG shows molecular phosphate incorporated into GST-cGB-pDE5 protein on a one-to-one ratio.

A cGMP binding assay for compounds of interest (Francis S. H. et al, J. Biol. Chem. 255, 620–626, 1980) is done in a total volume of 100 $\mu L$ containing 5 mM sodium phosphate buffer (pH=6.8), 1 mM EDTA, 0.25 mg/mL BSA, $H^3$-cGMP (2 $\mu M$, NEN) and the GST-cGB-PDE5 fusion protein (30 pg /assay). Each compound to be tested is added at the same time as $^3$H-cGMP substrate, and the mixture is incubated at 22° C. for 1 hour. Then, the mixture is transferred to Brandel MB-24 cell harvester with GF/B as the filter membrane followed by 2 washes with 10 mL of cold 5 mM potassium buffer(pH 6.8). The membranes are then cut out and transferred to scintillation vials followed by the addition of 1 mL of $H_2O$ and 6 mL of Ready Safe™ liquid scintillation cocktail to each vial. The vials are counted on a Beckman LS 6500 scintillation counter.

For calculation, blank samples are prepared by boiling the binding protein for 5 minutes, and the binding counts are <1% when compare to unboiled protein. The quenching by filter membrane or other debris are also calibrated.

PDE5 inhibitors, sulindac sulfide, exisulind, E4021 and zaprinast, and cyclic nucleotide analogs, cAMP, cyclic IMP, 8-bromo-cGMP, cyclic UMP, cyclic CMU, 8-bromo-cAMP, 2'-O-butyl-cGMP and 2'-O-butyl-cAMP were selected to test whether they could competitively bind to the cGMP binding sites of the GST-cGB-pDE5 protein. cGMP specifically bound to GST-cGB-PDE5 protein. Cyclic AMP, cUMP, cCMP, 8-bromo-cAMP, 2'-O-butyl-cAMP and 2'-O-butyl-cGMP did not compete with cGMP in binding. Cyclic IMP and 8-bromo-cGMP at high concentration (100 $\mu$M) can partially compete with cGMP (2 $\mu$M) binding. None of the PDE5 inhibitors showed any competition with cGMP in binding of GST-cGB-PDE5. Therefore, they do not bind to the cGMP binding sites of PDE5.

However, Compound 38 does competitively (with cGMP) bind to PDE 5. Given that Compound 38 does not bind to the cGMP-binding site of PDE5, the fact that there is competitive binding between Compound 38 and cGMP at all means that desirable compounds such as Compound 38 bind to the cGMP catalyic site on PDE5, information that is readily obtainable by one skilled in the art (with conventional competitive binding experiments) but which can assist one skilled in the art more readily to model other compounds. Thus, with the chemical structures of desirable compounds presented herein and the cGMP binding site information, one skilled in the art can model, identify and select (using the selection criteria of this invention) other chemical compounds for use as therapeutics.

Examples of compounds that inhibit PDE2 and PDE5 (with insubstantial COX inhibition) include exisulind and compounds disclosed in U.S. Pat. Nos. 5,965,619 and 6,063,818 which are incorporated herein by reference.

BIOLOGICAL EFFECTS (A) Cyclooxygenase (COX) Inhibition

COX catalyzes the formation of prostaglandins and thromboxane by the oxidative metabolism of arachidonic acid. The compound of Example 1 of this invention, as well as a positive control, (sulindac sulfide) were evaluated to determine whether they inhibited purified cyclooxygenase Type I (see Table 1 below).

The compounds of this invention were evaluated for inhibitory effects on purified COX. The COX was purified from ram seminal vesicles, as described by Boopathy, R. and Balasubramanian, J., 239:371–377, 1988. COX activity was assayed as described by Evans, A. T., et al., "Actions of Cannabis Constituents on Enzymes Of Arachidonate Metabolism Anti-Inflammatory Potential," Biochem. Pharmacol., 36:2035–2037, 1987. Briefly, purified COX was incubated with arachidonic acid (100 $\mu$M) for 2.0 min at 37° C. in the presence or absence of test compounds. The assay was terminated by the addition of TCA, and COX activity was determined by absorbance at 530 nm.

TABLE 1

| EXAMPLE | COX I<br>% Inhibition(100 $\mu$M) |
|---|---|
| Sulindac sulfide | 86 |
| 1 | <25 |

The advantage of very low COX inhibition is that compounds of this invention can be administered to patients without the side effects normally associated with COX inhibition.

(B) cGMP PDE Inhibition

Compounds of this invention are also PDE2 and PDE5 inhibitors as taught in part U.S. patent application Ser. No. 09/046,739 filed Mar. 24, 1998. Compounds can be tested for inhibitory effect on phosphodiesterase activity using either the enzyme isolated from any tumor cell line such as HT-29 or SW-480. Phosphodiesterase activity can be determined using methods known in the art, such as a method using radioactive $^3$H cyclic GMP (cGMP)(cyclic 3',5'-guanosine monophosphate) as the substrate for PDE5 enzyme. (Thompson, W. J., Teraski, W. L., Epstein, P. M., Strada, S. J., Advances in Cyclic Nucleotide Research, 10:69–92, 1979, which is incorporated herein by reference). In brief, a solution of defined substrate $^3$H-cGMP specific activity (0.2 $\mu$M; 100,000 cpm; containing 40 mM Tris-HCl (pH 8.0), 5 mM MgCl$_2$ and 1 mg/ml BSA) is mixed with the drug to be tested in a total volume of 400 $\mu$l. The mixture is incubated at 30° C. for 10 minutes with partially purified cGMP-specific PDE isolated from HT-29 cells. Reactions are terminated, for example, by boiling the reaction mixture for 75 seconds. After cooling on ice, 100 $\mu$l of 0.5 mg/ml snake venom (O. Hannah venom available from Sigmna) is added and incubated for 10 min at 30° C. This reaction is then terminated by the addition of an alcohol, e.g. 1 ml of 100% methanol. Assay samples are applied to a anion chromatography column (1 ml Dowex, from Aldrich) and washed with 1 ml of 100% methanol. The amount of radioactivity in the breakthrough and the wash from the columns in then measured with a scintillation counter. The degree of PDE5 inhibition is determined by calculating the amount of radioactivity in drug-treated reactions and comparing against a control sample (a reaction mixture lacking the tested compound).

Using such protocols, the compound of Example 1 had an IC$_{50}$ value for PDE5 inhibition of 0.68 $\mu$M. Using similar protocols, the compound of Example 38 ("Compound 38") had an IC$_{50}$ value for PDE2 of 14 $\mu$M, an IC$_{50}$ value for PDE5 of 4 $\mu$M, an IC$_{50}$ value for PDE1 of 3 $\mu$M, and an IC$_{50}$ value for PDE4 of 6 $\mu$M.

(C) Safety Assessment in Mammals

As one skilled in the art will recognize from the data presented below, Compound 38 can safely be given to animals at doses far beyond the tolerable (and in many cases toxic) doses of non-insulin type I diabetes therapies. For example, in an acute toxicity study in rats, single oral doses of Compound 38 administered (in a 0.5% carboxymethyl-cellulose vehicle) at doses up to and including 2000 mg/kg resulted in no observable signs of toxicity. At 2000 mg/kg, body weight gains were slightly reduced. A single dose of 1000 mg/kg administered intraperitoneally resulted in reduced body weight gain, with mesenteric adhesions seen in some animals from this group at necropsy.

In dogs, the administration of Compound 38 in capsules at 1000 mg/kg resulted in no signs of toxicity to the single group of two male and two female dogs. Due to the nature of Compound 38 capsules, this dose necessitated the use of at least 13 capsules to each animal, which was judged to be the maximum number without subjecting the animals to stress. Therefore, these dogs were subsequently administered seven consecutive doses of 1000 mg/kg/day. At no time in either dosing phase were any obvious signs of drug-related effects observed.

Thus, on a single-dose basis, Compound 38 is not acutely toxic. Based on the findings of these studies, the oral LD$_{50}$ of Compound 38 was considered to be greater than 1000 mg/kg in dogs and 2000 mg/kg in rats, and the intraperitoneal LD$_{50}$ was considered to be greater than 1000 mg/kg in rats.

A seven-day dose-range finding study in rats, where Compound 38 was evaluated by administering it at doses of 0, 50, 500 or 2000 mg/kg/day resulting in no observable signs of toxicity at 50 mg/kg/day. At 500 mg/kg/day, treatment-related effects were limited to an increase in absolute and relative liver weights in female rats. At 2000 mg/kg/day, effects included labored breathing and/or abnormal respiratory sounds, decreased weights gains and food consumption in male rats, and increased liver weights in female rats. No hematological or blood chemistry changes nor any microscopic pathology changes, were seen at any dose level.

A 28-day study in rats was also carried out at 0, 50, 500 and 2000 mg/kg/day. There were no abnormal clinical observations attributed to Compound 38, and body weight changes, ophthalmoscopic examinations, hematological and blood chemistry values and urinalysis examinations were unremarkable. No macroscopic tissue changes were seen at necropsy. Organ weight data revealed statistically significant increase in liver weights at 2000 mg/kg/day, and statistically significant increases in thyroid weights for the 2000 mg/kg/day group. The slight liver and thyroid increases at the lower doses were not statistically significant. Histopathological evaluation of tissues indicated the presence of traces of follicular cell hypertrophy, increased numbers of mitotic figures (suggestive of possible cell proliferation) in the thyroid gland and mild centrilobular hypertrophy in the liver. These changes were generally limited to a small number of animals at the 2000 mg/kg/day dose, although one female at 500 mg/kg/day had increased mitotic figures in the thyroid gland. The findings in the liver may be indicative of a very mild stimulation of liver microsomal enzymes, resulting in increased metabolism of thyroid hormones, which in turn resulted in thyroid stimulation.

A long-term safety assessment study was conducted in rats to investigate Compound 38 at 50, 200 and 500 mg/kg/day following repeated oral dosing for 91 consecutive days. Orally administered Compound 38 did not produce any major toxicological effects in rats. The only finding was a dose-related trend to increased liver and thyroid/parathyroid weights noted in males and females at 200 and 500 mg/kg/day. Microscopically, slight hepatocellular hypertrophy at 200 and 500 mg/kg/day groups, follicular cell hypertrophy at 500 mg/kg/day and increase in accumulation of hyalin droplets in the kidneys at 200 and 500 mg/kg/day group. However, no changes in clinical biochemistry and hematology were evident. These changes were not associated with any gross clinical abnormality.

Dogs were also dosed orally with Compound 38 at 50, 150 and 300 mg/kg/day for 91 consecutive days. There were no toxicological effects in the dog following 91 days of dosing. Orange discoloration of the feces (same color as Compound 38) was seen in the 150 and 300 mg/kg/day groups. This finding suggested that most of Compound 38 was being eliminated via the feces. Slightly lowered body weights were noted in the highest dose group. This dose was also associated with increased liver weights. However, there were no microscopic alterations to support the increase in liver weight. Therefore, we concluded that Compound 38 is well tolerated in the dog.

Finally as to safety, in a single, escalating dose human clinical trial, patients, human safety study in which the drug was taken orally, Compound 38 produced no significant side effects at any dose (i.e., 50 mg BID, 100 mg BID, 200 mg BID and 400 mg BID).—doses above the level believed to be therapeutic for human patients. One skilled in the art should recognize that any of the side effects observed in these safety studies occurred at very high doses, in excess of recommended human doses and are extremely minimal compared to what one would expect at similar doses of other proposed therapies.

(D) Efficacy for Type I Diabetes i. Macrophage Involvement

As mentioned above, macrophages have been implicated in the progression of Type I diabetes (see Jansen et al., *Diabetes* Vol. 43, No. 5 pp. 667–675 (1994)). Specifically, macrophages have been found to invade pancreatic tissue including the islets and their surrounding tissue in many animal models of diabetes including the BB/E rat and NOD mouse (see Walker et al., Diabetes, Vol. 37 No. 9 pp. 1301–04 (1988) and Jun et al., *Diabetes*, Vol. 48, No. 1, pp. 34–42 (1999)). The invading activated macrophages play critical roles in the pathological events of IDDM progression.

As demonstrated below, we found that macrophages contain PDE2 and PDE5, and the inhibition of PDE2 particularly with PDE5 inhibition leads to apoptosis of macrophage cells. We believe the administration of a PDE2 inhibitor can treat the progression of Type I diabetes, particularly when PDE5 is also inhibited.

ii. PDE2 and PDE5 MRNA Levels in Treated and Untreated U937 Cells by RT-pCR

The U937 monocyte cell line was derived from a histocytic lymphoma and can be driven to differentiate into an 'activated macrophage like' state by treatment with 5 nM phorbal ester (TPA). Treated U937 cells become adherent, increase their cytoplasmic volume and express macrophage-specific cell surface markers. The presence and level of PDE2 and 5 MRNA in both differentiated and non-differentiated U937 cells was confumed by performing RT-pCR experiments on total RNA.

U937 cells (from ATCC Rockville, Md.) were grown in RPMI media supplemented with 5% FCS, glutamine, antibiotic/antimycotic and sodium pyruvate. Total RNA was isolated from two U937 cultures, one treated with 5 nM TPA for 48 hours and one grown in normal media as listed above, using the Rouche High Pure RNA Isolation Kit (cat #1 828 665) as per manufacturers protocol. cDNA was then synthesized from the total RNA using GibcoBRL SuperscriptII (Cat #18064-022) reverse transcriptase as per manufacturers protocol. The resulting cDNA was used as a template for RT-PCR reactions using primer sets specific for PDE2 (forward: CCCAAAGTGGAGACTGTCTACACCTAC, reverse: CCGGTTGTCTTCCAGCGTGTC) or PDE5 (forward: GGGACTTTACCTTCTCATAC, reverse: GTGACATCCAAATGACTAGA). mRNA for PDE2 and 5 were both present in the untreated U937 cells. Upon treatment with TPA, the relative amounts of PDE2 mRNA increased 5 fold. Therefore, U937 cells treated with TPA and driven to differentiate into an activated macrophage like state have elevated levels of PDE2 mRNA (see FIG. 1).

iii. Confirmation of PDE2 and PDE5 Protein Within U937 Cells by Indirect Immunofluorescence The presence of PDE2 and PDE5 protein within U937 cells was confirmed by indirect immunofluorescence (IIF). U937 cells were cultured as above. Two U937 cultures, one grown in the presence of 5 nM TPA for 48 hours and one grown in normal media were processed. All cultures were collected by centrifugation (Shandon Cytospin, 2 minutes @600 rpm) onto poly-L lysine-coated slides and immediately fixed in fresh 3% paraformaldehyde buffered in PBS for 10 minutes. Adherent cultures were grown on coverslips and fixed as above. Cells were permeablized in 0.2% Triton-100 for 2 minutes. Slides were blocked with blocking buffer (5% goat serum, 5% glycerol, 1% gelatin from cold water fish skin and 0.04% $NaN_3$ in PBS) for 1 hour at room temperature.

Slides were then incubated for 1 hour at 37° C. in a humid chamber with antibodies specific for PDE2 (generated in a sheep against the peptide TLAFQKEQKLKCECQA) or PDE5 (generated in sheep against the peptide CAQLYETSLLENKRNQV). The PDE5 antibody was used at a dilution of 1:200 and the PDE2 antibody was used at a dilution of 1:100. All dilutions were performed in blocking buffer. Slides were then washed 2× for 10 minutes each in PBS and then incubated with a Cy3 conjugated secondary antibody (Jackson ImmunoResearch laboratories, Inc. Cat. #713-166-147) diluted 1:1000 in blocking buffer, for 1 hour at 37° C. in a humid chamber. Slides were then washed 2× for 10 minutes each in PBS and counterstained with DAPI (5 ng/ml) and mounted in VectaShield. Digital images were then obtained using a SPOT-2 camera and an Olympus IX-70 fluorescent microscope. Both PDE2 and PDE5 are present in the cytoplasm of U937 cells. There is an increase in the level of both PDE2 and PDE5 in TPA-treated U937 cells. These increased protein levels are seen in discrete perinuclear foci (see FIGS. 2 through 5).

iv. Cyclic GMP Hydrolysis Within U937 Cells cGMP-hydrolytic activity in TPA-treated and untreated U937 cells was determined by performing a permeablized cell assay and direct analysis of enzyme activity in protein lysates. Both procedures achieved similar results, namely, elevated activity in the treated cells compared to untreated cells.

Figure 6:
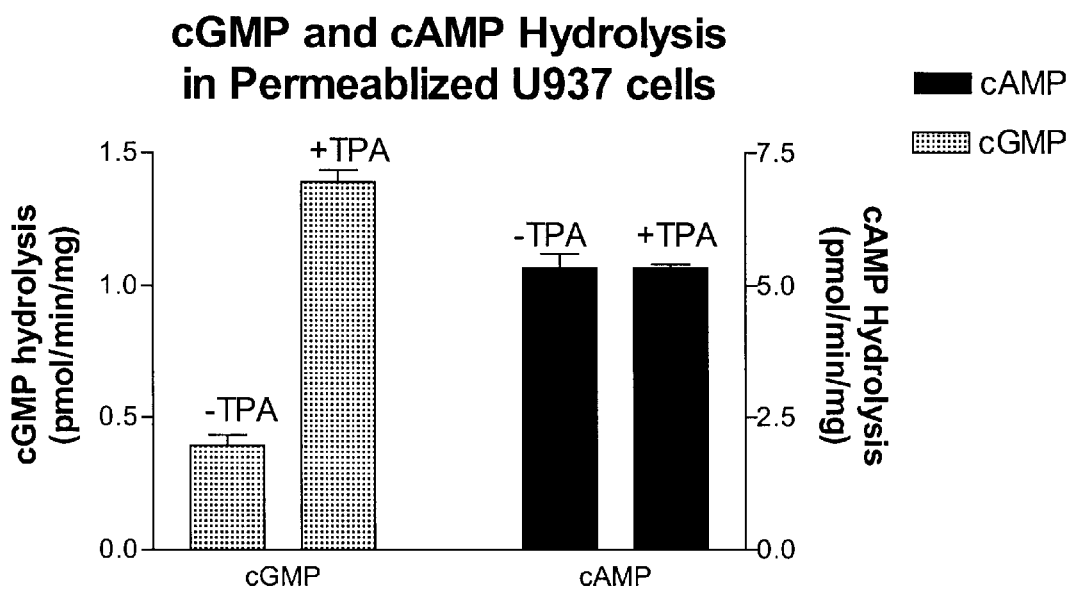
FIG. 6 is a graph that illustrates cGMP and cAMP hydrolysis levels in activated and control macrophages.
Figure 7:
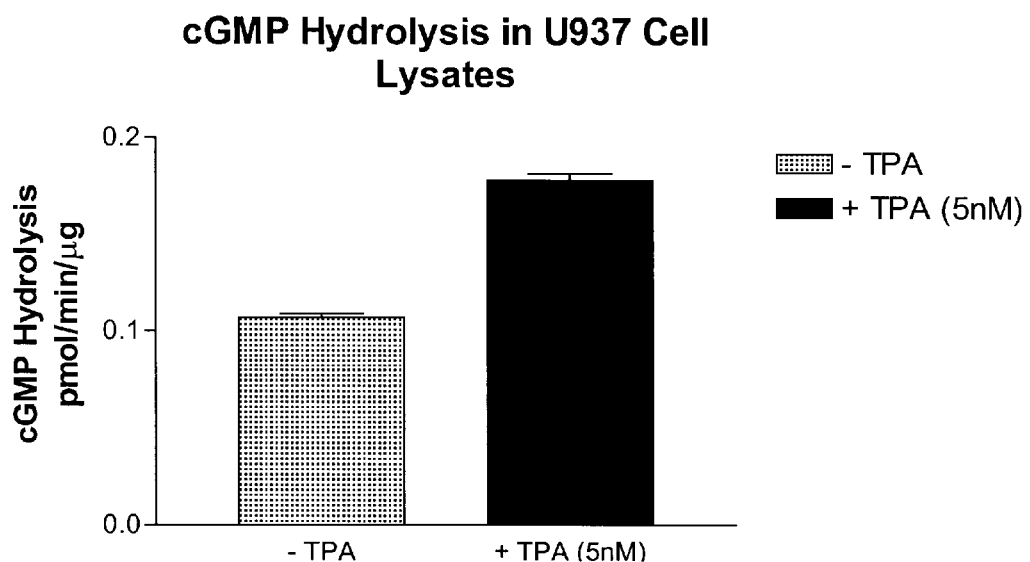
FIG. 7 is a graph that illustrates cGMP hydrolysis levels in protein lysates from activated and control macrophages.

The cGMP hydrolysis levels in permeablized U937 cells was performed by washing the cells for 5 minutes with DMEM followed by cold PBS. Cells were then placed on ice in 700 $\mu$l ice cold Tris-HCL buffer (20 mM; pH 7.4) containing $MgCl_2$ (5 mM) 0.5% Triton X-100, and protein inhibitors (10 mM bezamidine, 10 $\mu$M TLDK, 2000 U/ml aprotinin, 2 $\mu$M leupeptin, 2 $\mu$M pepstatin A). The reaction was initiated by the addition of 100 pl of 0.5 mg/ml snake venom and 0.25 $\mu$M cGMP or cAMP along with [$^3$H]cGMP or [$^3$H]cAMP, respectively. After incubating for 30 minutes at 30° C. the reactions were terminated by the addition of 1.8 ml methanol. The extract was then applied to a 1 ml Dowex anion exchange column to remove unreacted substrate. The eluant was collected and counted in 6 ml scintillation fluid. As shown in FIG. 6, U937 cell cGMP hydrolysis levels elevate when the cells are driven into an activated macrophage-like state upon treatment with TPA, as compared to unactivated, untreated cells.

cGMP hydrolysis levels in protein lysates extracted from TPA-treated and untreated U937 cells were also analyzed as follows. Cells were resuspended in 20 mM TRIS-HCl, 5 mM MgCl2, 0.5% Triton X-100, 0.1 mM EDTA, 10 mM benzamidine, 10 $\mu$M TLCK, 20 nM aprotinin, 2 $\mu$M leupeptin, 2 $\mu$M pepstatin A, pH 8.0 were added. The cells were homogenized using a glass tissue grinder and teflon pestle. Samples were ultracentrifuged at 100,000×g for 1 hr at 0° C. Supernatants were assayed at 0.25 $\mu$M cGMP using the method from Thompson, W. J. et. al. Adv. Cyclic Nucleotide Res., 10: 69–92, 1979. Again, the level of cGMP hydrolytic activity increased upon TPA treatment/activation, compared with no treatment/unactivation (see FIG. 7). Both of these experiments corroborate the results of our experiments above that show that both cGMP PDE2 and PDE5 protein levels increase in U937 cells treated with TPA.

v. Apoptosis Induction of U937 Cells by Compound 38

Figure 8:
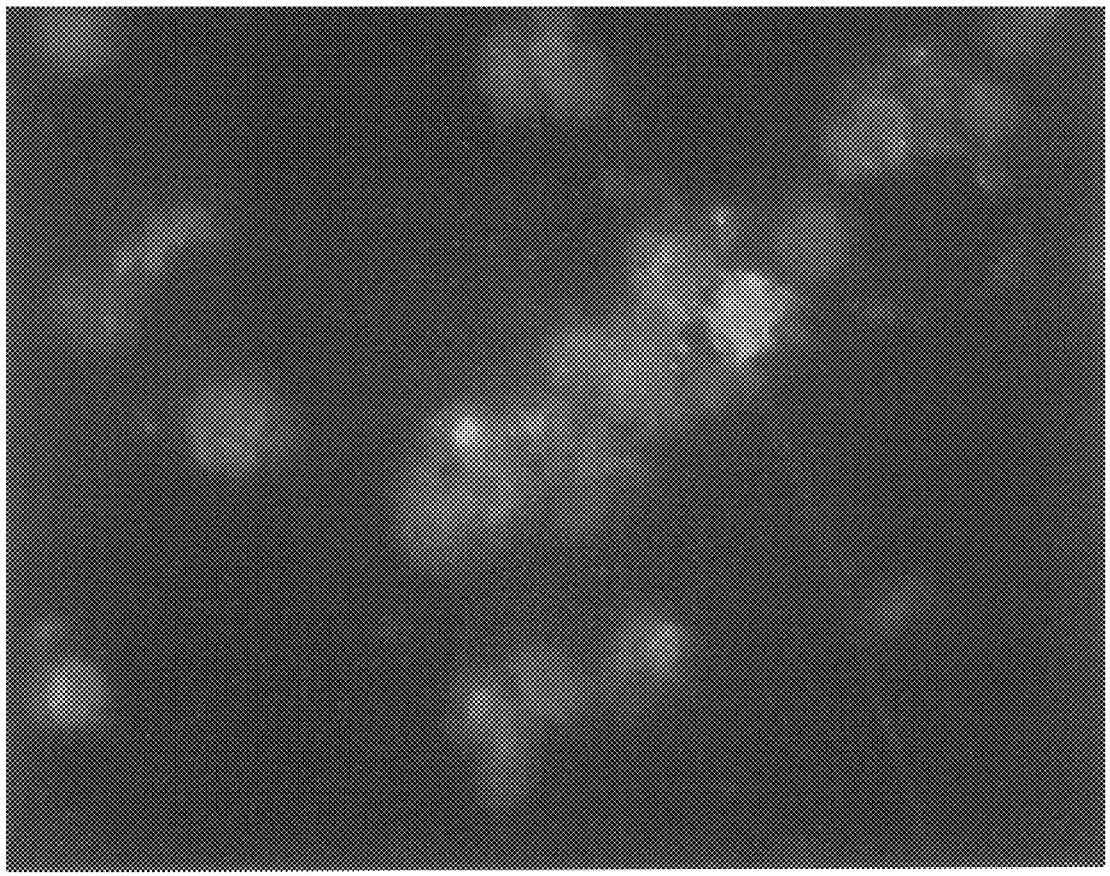
FIG. 8 is a digital image obtained with a fluorescent microscope of activated macrophages treated with a PDE2 inhibitor wherein the macrophages undergo apoptosis as reflected by the presence of active caspase 3 (red signal).
Figure 9:
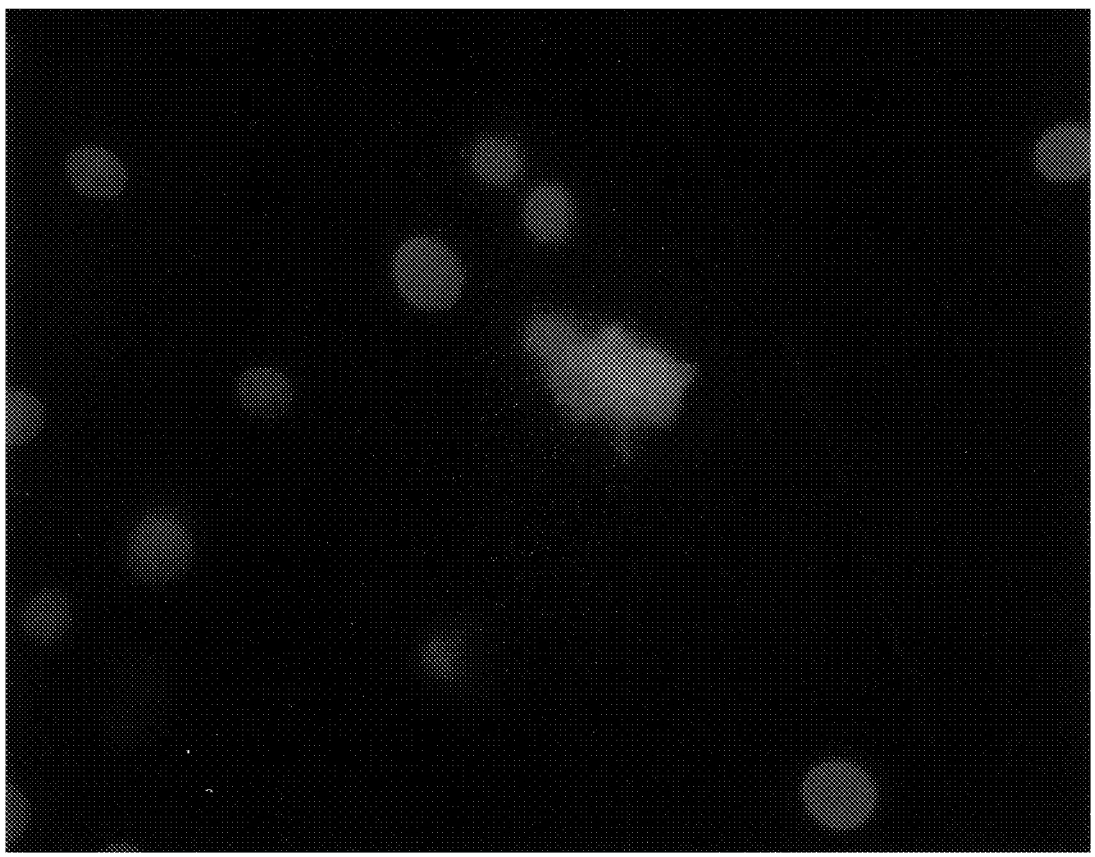
FIG. 9 is a digital image obtained with a fluorescent microscope of control (vehicle only) macrophages revealing only low, background levels of apoptosis as reflected by the reduced presence of active caspase 3 (red signal).

U937 cells were cultured, as described above, with and without treatment with 5 nM TPA for 24 hours at which time the cultures were treated either with 1 $\mu$M Compound 38 or vehicle (DMSO) alone for an additional 24 hours. Adherent cells were dislodged by treatment with trypsin EDTA for 5 minutes at 37° C. Cells were then processed for IIF as described above, except that an antibody specific for active caspase 3 was used (as per manufacturer's protocol) instead of antibodies to PDE2 or 5 (Promega Cat. #G7481). The anti-active caspase 3 antibody was diluted 1:200 in blocking buffer and processed according to the manufacturer's protocol. The resulting slides were observed under a fluorescent microscope and a digital images were obtained. FIG. 8 shows U937 cells treated with 1 $\mu$M compound 38 undergoing apoptosis as reflected by the presence of active caspase 3 (red signal). Image of control (vehicle only) U937 cells reveals only low, background levels of apoptosis (FIG. 9).

The level of apoptosis in U937 cells was quantified by scoring 500 consecutive cells for the presence of active caspase 3. These results are summarized in the following table.

| Cell type | TPA treatment | Compound 38 | Number of apoptotic cells | Percentage of apoptotic cells |
|---|---|---|---|---|
| U937 | | | 6/500 | 1.2% |
| U937 | | 1 $\mu$M, 24 hrs | 375/500 | 75% |
| U937 | 5 nM, 16 hrs | | 59/500 | 11.8% |
| U937 | 5 nM, 16 hrs | 1 $\mu$M, 24 hrs | 392/500 | 78% |

Therefore, compound 38 causes the induction of apoptosis in the differentiated and non-differentiated U937 cell line.

vi. Treatment of U937 Cells With Either Sildenafil (PDE5-Specific Inhibitor) or Rolipram (PDE4-Specific Inhibitor) Does Not Induce Apoptosis.

The activity of specific PDE inhibitors contrast with the activity of compound 38 in U937 cells. By "specific" in this context, we mean the other PDE inhibitors that inhibited one PDE primarily, but not several PDEs (e.g., inhibiting PDE2 and PDE5 at roughly the same concentration). An example is sildenafil, which primarily inhibits PDE5, and only at much higher concentrations may only marginally inhibit other PDEs. Another example is rolipram (PDE4-specific).

Figure 10:
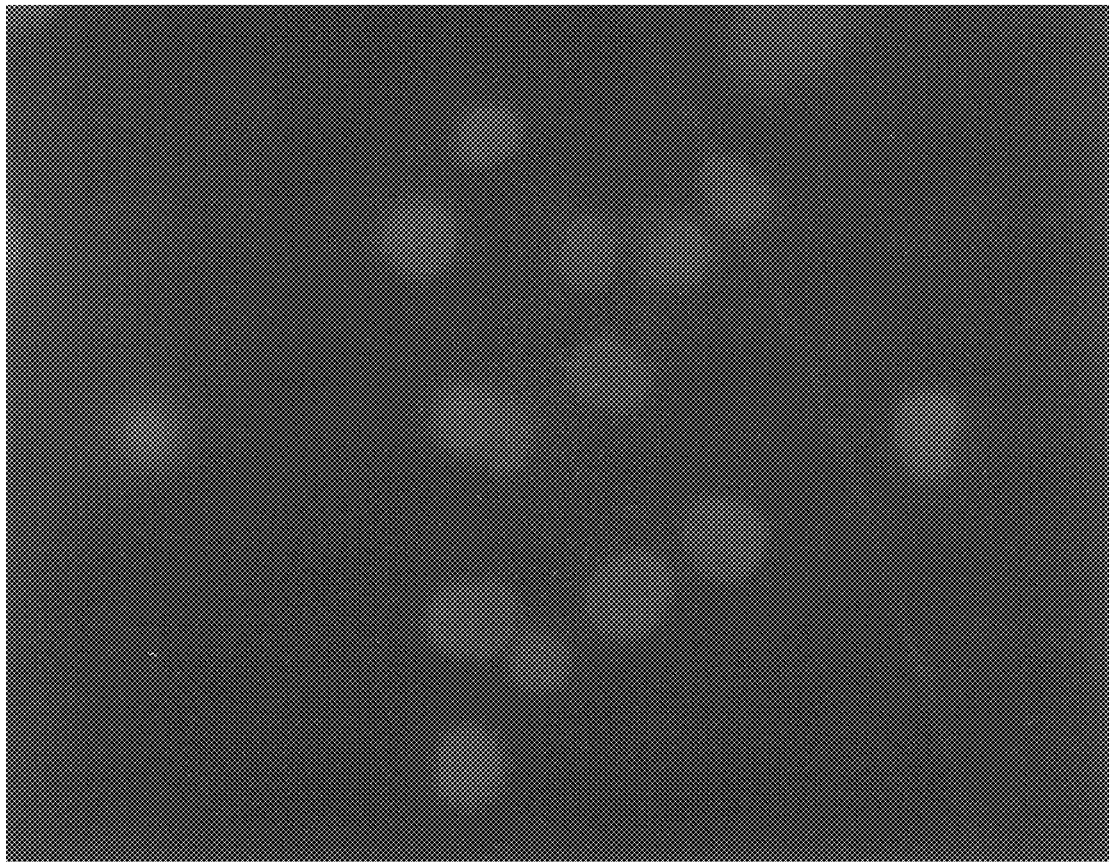
FIG. 10 is a digital image obtained with a fluorescent microscope of activated macrophages treated with a PDE4-specific inhibitor wherein the macrophages do not undergo substantial apoptosis as reflected by the substantial absence of active caspase 3 (red signal).
Figure 11:
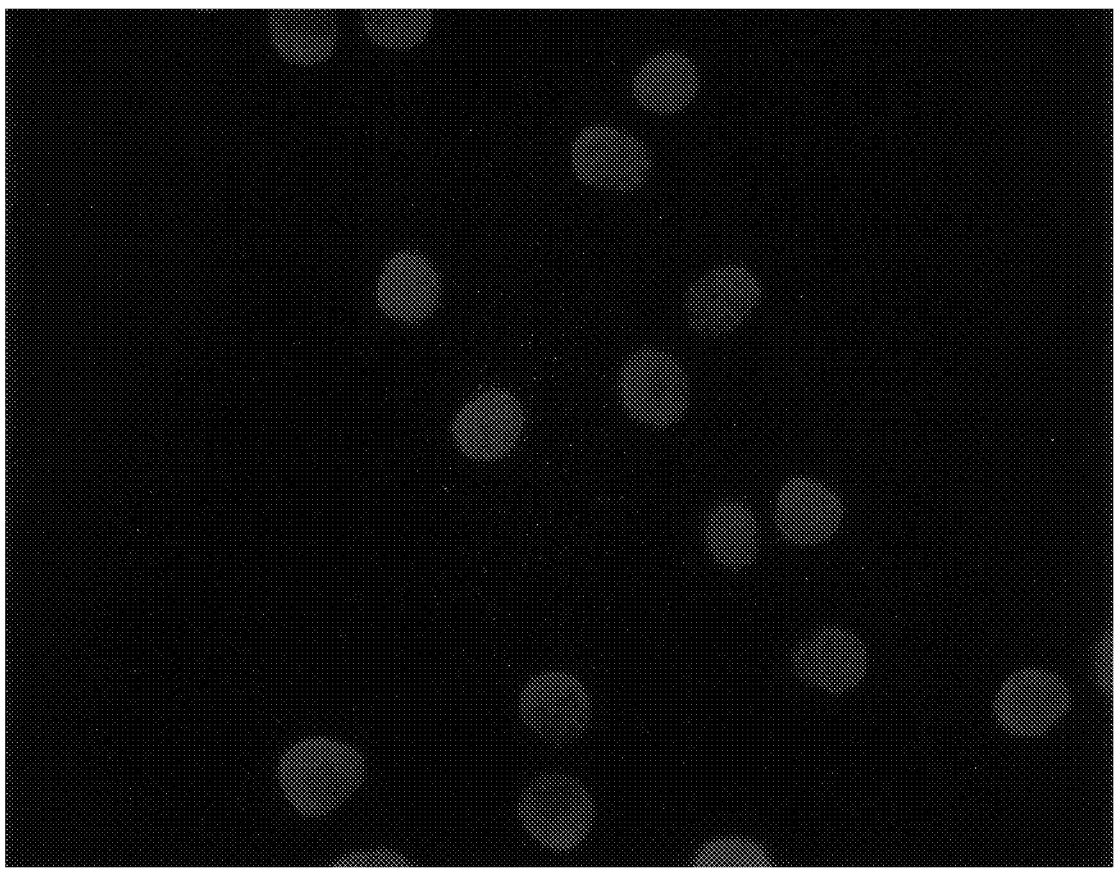
FIG. 11 is a digital image obtained with a fluorescent microscope of activated macrophages treated with a PDE5-specific inhibitor wherein the macrophages do not undergo substantial apoptosis as reflected by the substantial absence of active caspase 3 (red signal).

U937 cells were incubated in the presence of 0.3 nM sildenafil or 0.5 uM rolipram for 24 hours using the culture conditions described above. The cells were harvested and processed for IIF as described above using an antibody that specifically recognizes active caspase 3. Digital images are shown in FIGS. 10 and 11. No increase in the levels of apoptosis compared to normal background was observed. Therefore, the inhibition of only PDE4 or PDE5 alone (i.e. without the inhibition of PDE2) is not sufficient to induce apoptosis in U937 cells.

vii. Compound 38 Decreases TNF Alpha Levels in U937 Media

One function of macrophages is to modulate the activity of other inflammatory cells through various cytokine molecules. We therefore tested the effect of compound 38 on the ability of U937 cells to produce and secrete tumor necrosis factor-α (TNF-α). This was done by performing an immunoassay on the cell culture media taken from differentiated U937 cells (TPA treated) grown in the presence or absence of compound 38.

Figure 12:
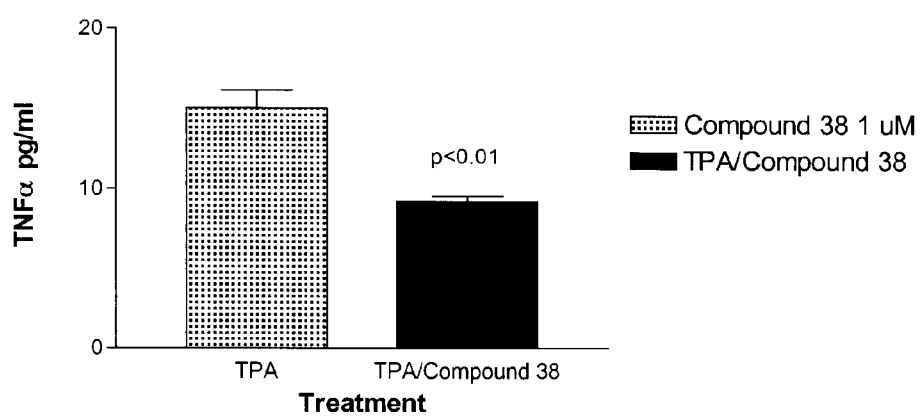
FIG. 12 is a graph illustrating decreased TNFα levels in activated macrophages with exposure to a PDE2 inhibitor.

TNF-α levels in the cell culture media were determined by using the TNF-α Immunoassay from R&D Systems (Cat. #DTA50) according to the manufacturer's protocol. As shown in FIG. 12, Compound 38 treatment significantly reduced the level of TNF-α secreted by TPA-induced U937 cells.

viii Phosphodiesterase and Macrophage Involvement In A Type I Diabetes Animal Model BBDP/Wor and BBDR/Wor Rats The BB/Wor rat develops spontaneous and viral-induced syndromes of auto-immune diabetes mellitus, and reportedly is the best rat model of human Type 1 diabetes. Salient features include: genetic predisposition, abrupt onset of insulin dependent, ketosis-prone diabetes, and auto-immune destruction of pancreatic β-cells. Since the first description of the syndrome in 1977, more than one thousand papers have been published by laboratories throughout the world. Support for the immune pathogenesis of diabetes in the BB/Wor rat is derived from the following: lymphocytic insulitis prior to and during the acute onset of hyperglycemia; selective destruction of the pancreatic β-cells with sparing of the other islet cells; prevention and/or amelioration of β-cell destruction by immune suppressive agents directed against T cells and macrophages, and measures which correct the effects of genetically induced T cell lymphopenia; adoptive transfer insulitis and diabetes to naive recipients with Conconavalin-A (CON-A) activated acute diabetic spleen cells. Other features of the BB/Wor rat which identify it as the best rat model of human IDDM include their inbred status (>75 generations of sib matings) and high (80–95%) incidence of diabetes among both genders, and an average age onset of diabetes at 70 days.<O:P></O:P>

Pancreatic tissue was collected from three BBDP/Wor female rats characterized as having diabetes mellitus (type I diabetes). Animals were randomized into three groups (n=1) and were characterized phenotypically into prone- (early stage disease), acute-(mid-stage disease) and chronic- (late-stage disease, insulin-dependent) stage type I diabetes. In addition, three age-matched resistant controls (BBDR/Wor) were included into the study.

Phosphodiesterase Labeling Procedure

The BBDP/Wor rat pancreatic tissue specimens were fixed in 10% buffered formalin, paraffin embedded, sectioned at 5 μm and stored at room temperature in a slide box until use. Sections were then dewaxed for 2 hours at 60° C. and deparaffinized in xylene, three incubations, two minutes each. Sections were rehydrated through an ethanol series at three different percentages (100, 95 and 70%), twice each for two minutes, followed by five minutes of rinsing in phosphate buffered saline. Endogenous peroxidase activity was blocked by incubating pancreatic sections in fresh 0.3% hydrogen peroxide at room temperature for 30 minutes. Sections were washed in phosphate buffered saline for 5 minutes, then blocked with blocking buffer (5% goat serum, 5% glycerol, 1% gelatin from cold water fish skin and 0.04% $NaN_3$ in phosphate buffered saline) for one hour. Tissue sections were incubated with primary antibody diluted in blocking buffer (affinity purified sheep anti-human PDE2(1), diluted 1:1500 and affinity purified sheep anti-human PDE5 (1), diluted 1:2000) and were incubated overnight at 4° C. in a humid chamber. Sections were washed three times for five minutes each in phosphate buffered saline. Sections were incubated with a secondary antibody (diluted donkey anti-sheep biotin conjugated immunoabsorbed antibody 1:2500) in blocking buffer, Jackson lmmunoResearch Catalog #713-065-147. Sections were then incubated at room temperature for 30 minutes, washed three times in phosphate buffered saline for 5 minutes. Diluted Vector ABC reagents were used as according to manufacture's protocol (vector Catalog #6106) and were incubated for 30 minutes at room temperature. Washed in phosphate buffered saline for 5 minutes. A DAB substrate kit was used per manufacture's protocol (Vector Catalog #SK-4100). Slides containing tissue were rinsed with distilled water and immediately immerse in Meyers hematoxylin for 1–5 minutes. Excess hematoxylin was rinsed off with distilled water. Slides were dipped 10 times in 2% glacial acetic acid solution followed by 10 dips in distilled water. Slides were incubated in bluing solution (15 mM ammonium water) 15 dips followed by 10 dips in water and dehydrated through an ethanol series. The labelled slides were then mounted in Permount (Sigma).

Macrophage Labeling Procedure

Rat tissue specimens were fixed in 10% buffered formalin, paraffin embedded, sectioned at 5 μm and stored at room temperature in a slide box until use. Sections were then dewaxed for 2 hours at 60° C. and deparaffinized in xylene, three incubations, two minutes each. Sections were rehydrated through an ethanol series at three different percentages, twice each for two minutes, followed by five minutes of rinsing in phosphate buffered saline. Endogenous peroxidase activity was blocked by incubating pancreatic sections in fresh 0.3% hydrogen peroxide at room temperature for 30 minutes. Sections were washed in phosphate buffered saline for 5 minutes, then blocked with blocking buffer (5% goat serum, 5% glycerol, 1% gelatin from cold water fish skin and 0.04% $NaN_3$ in phosphate buffered saline) for one hour. Tissue sections were incubated with primary antibody diluted in blocking buffer (anti-macrophage antibody, diluted 1:1000, Serotec Catalog #MCA341R.) and were incubated overnight at 4° C. in a humid chamber. Sections were washed three times for five minutes each in phosphate buffered saline. Sections were incubated with a secondary antibody (biotin anti-mouse antibody 1:2500) in blocking buffer. Sections were then incubated at room temperature for 30 minutes, washed three times in phosphate buffered saline for 5 minutes. Diluted Vector ABC reagents were used as according to manufacture's protocol (vector Catalog #6106) and were incubated for 30 minutes at room temperature. Washed in phosphate buffered saline for 5 minutes. A DAB substrate kit was used per manufacture's protocol (Vector Catalog #SK-4100). Slides containing tissue were rinsed with distilled water and immediately immerse in Meyers hematoxylin for 1–5 minutes. Excess hematoxylin was rinsed off with distilled water. Slides were dipped 10 times in 2% glacial acetic acid solution followed by 10 dips in distilled water. Slides were incubated in bluing solution (15 mM ammonium water) 15 dips followed by 10 dips in water and dehydrated through an ethanol series. The labelled slides were then mounted in Permount (Sigma).

Quantitative PDE2 and PDE5 Immunohistochemistry

Rat pancreatic tissues on microscope slides were analyzed by the Automated Cellular Imaging System (Chromavision, Capistrano, Calif.) using the generic DAB application (rev. A). Each tissue specimen was thoroughly scanned and 10 islet regions were examined and areas of necrosis were avoided. Percentage of cells with positive signal for PDE2 and PDE5 was computed. See table below for generated values (Table I under results section).

Quantitative Macrophage Immunohistochemistry Procedure

Beta islet regions of rat pancreatic tissue sections were microscopically observed with an Olympus light microscope (model #BX40), Olympus Optical CO., LTD, Japan. Objective lens used was 40× magnification. For each tissue section, approximately six beta islet regions were viewed for evidence of macrophages, and the total number of macrophages per tissue sample with positive signal was computed.

Areas of necrosis were avoided. See table II below under "results" for generated values.

Results

Figure 13A:
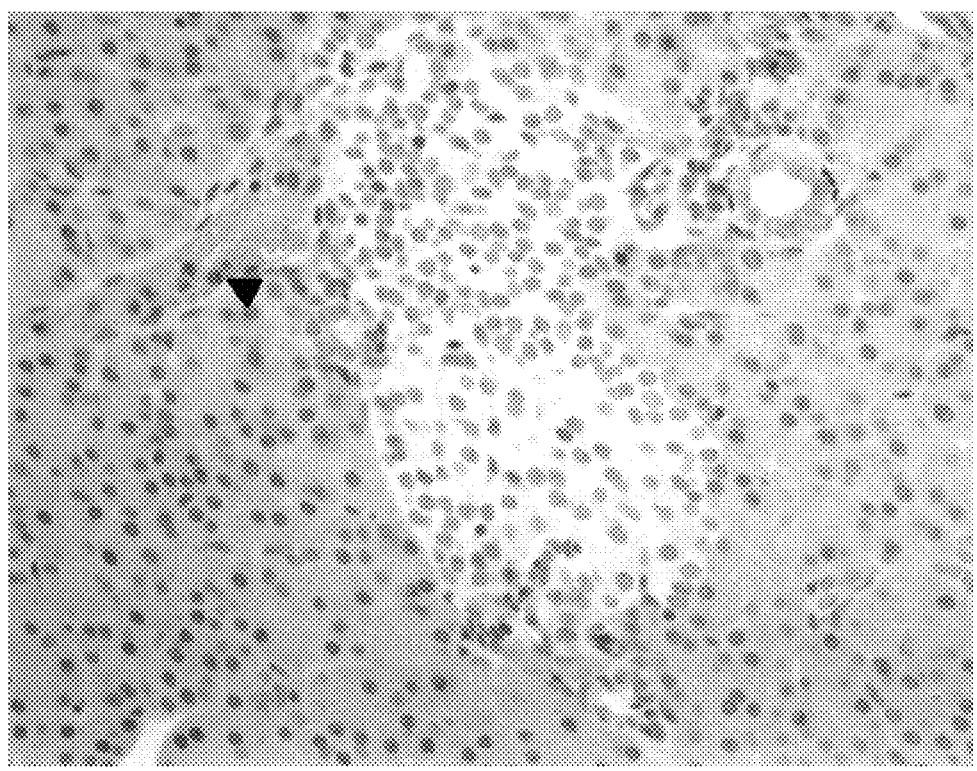
FIG. 13a is a photomicrograph of a regional islet zone in a BBDP/Wor rat (prone diabetic) pancreatic section where the positive brown stained tissue denotes activated macrophage homing toward the islet zone in a dilated capillary (arrowhead).
Figure 13B:
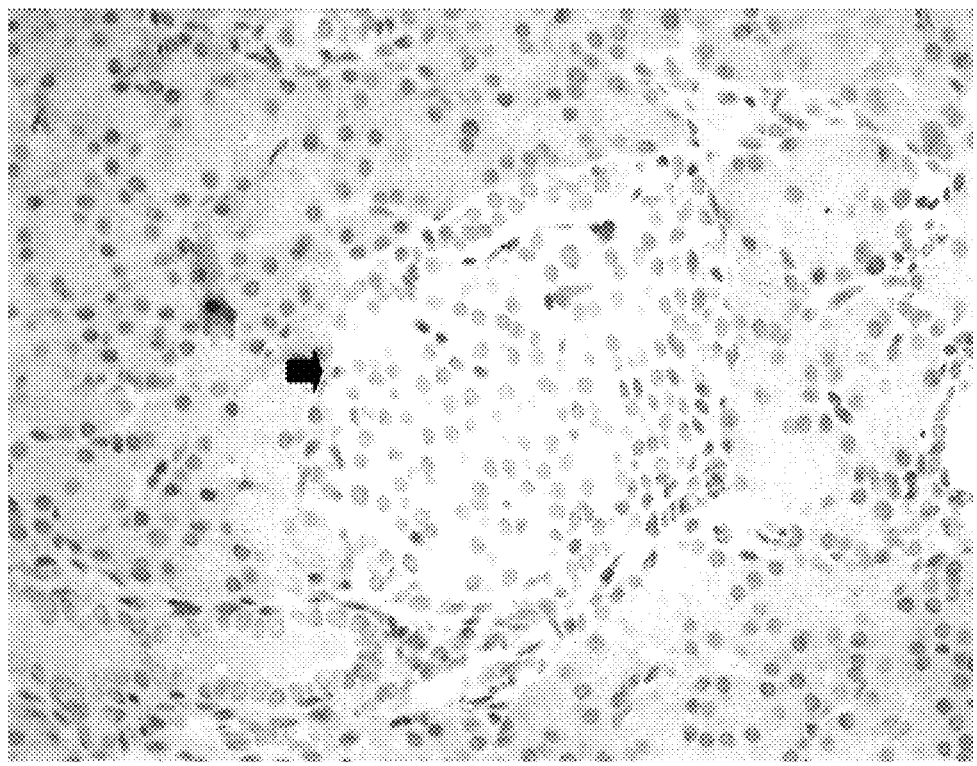

Microscopically, the prone BBDP/Wor rat pancreatic tissue displayed no positively stained macrophages in the islet region, however, early recruitment of activated macrophages were evident in vasodilated capillaries as photographed in FIG. 13a. Its prone-resistant, aged-matched control showed no pancreatic tissue-laden macrophages (FIG. 13b).

Figure 14A:
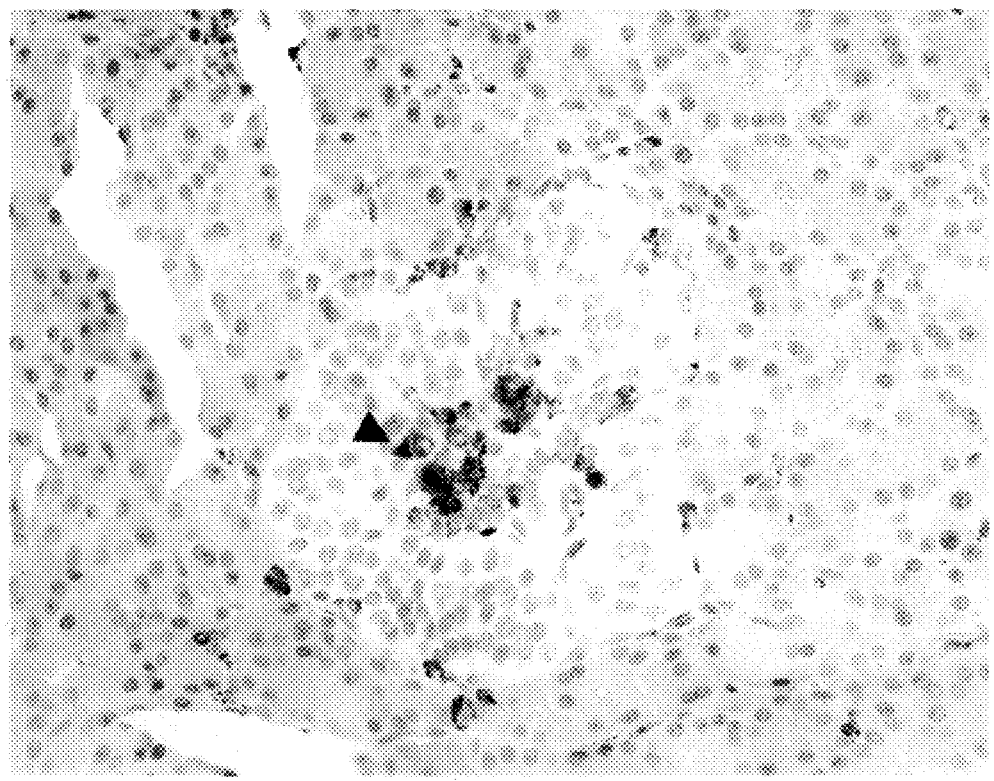
FIG. 14a is a photomicrograph of a regional islet zone in a BBDP/Wor rat (acute diabetic) pancreatic section where the positive brown stained tissue denotes activated macrophage in the islet region (arrowhead).
Figure 14B:
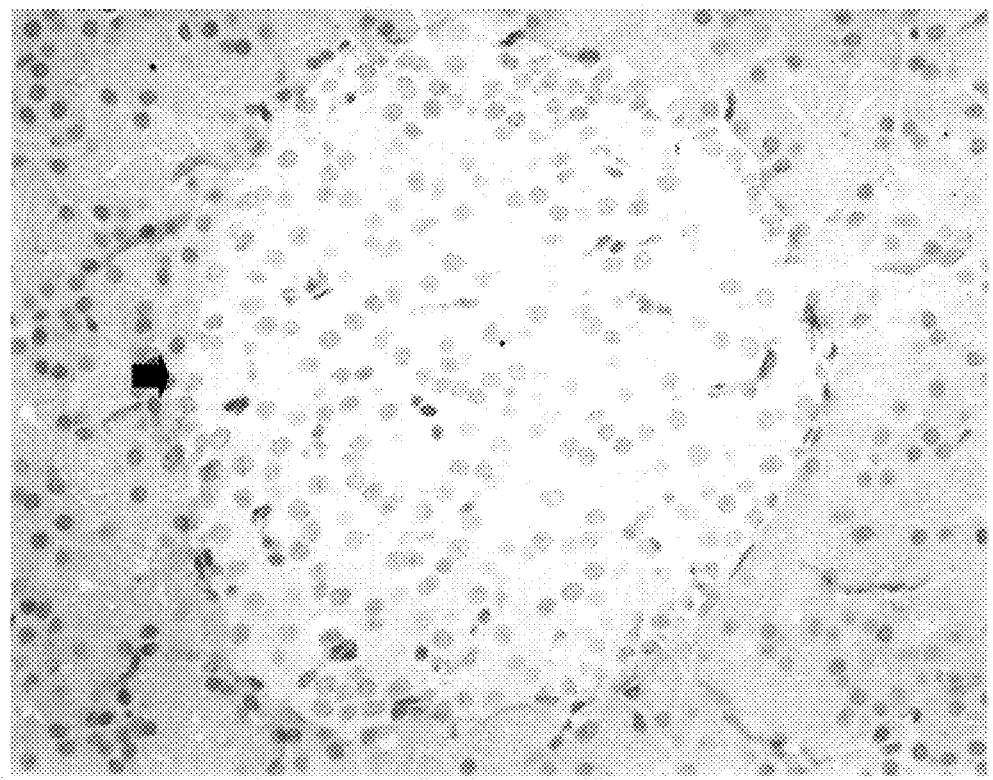

In contrast, following microscopic assessment, the highest number of tissue-activated macrophages was observed in the acute BBDP/Wor rat pancreas (FIG. 14a), and no macrophages were noted in the acute resistant, age-matched control (FIG. 14b).

Figure 15A:
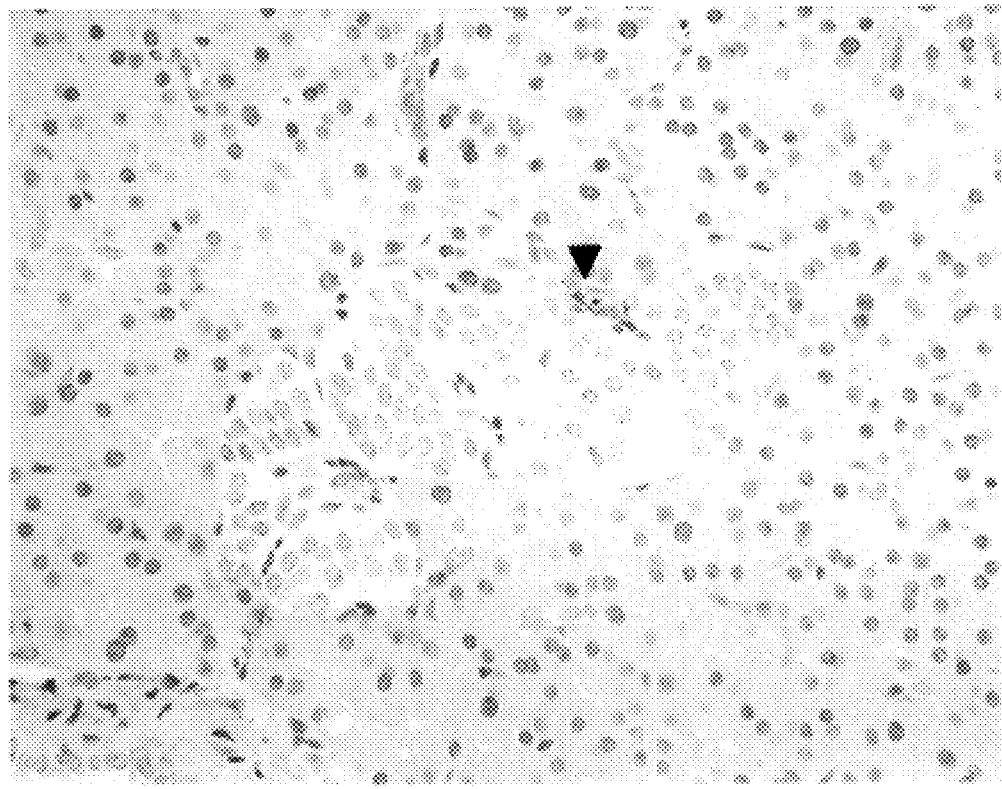
FIG. 15a is a photomicrograph of a regional islet zone in a BBDP/Wor rat (chronic diabetic) pancreatic section where the positive brown stained tissue denotes activated macrophage in the islet region (arrowhead).
Figure 15B:
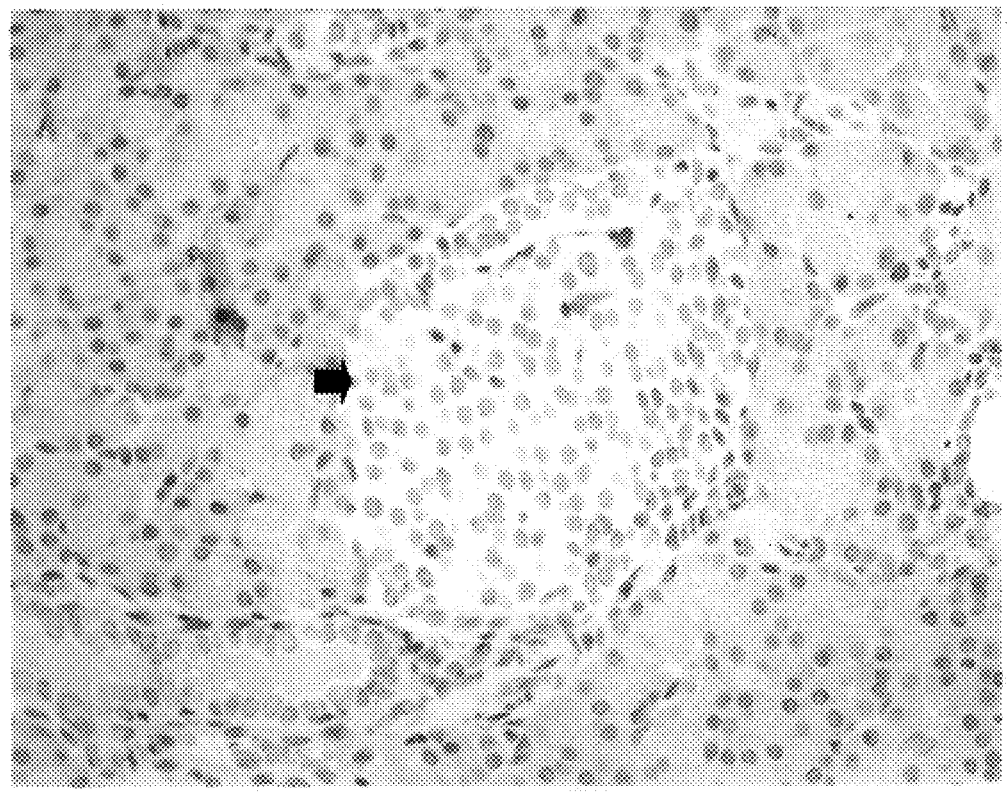
Figure 16:
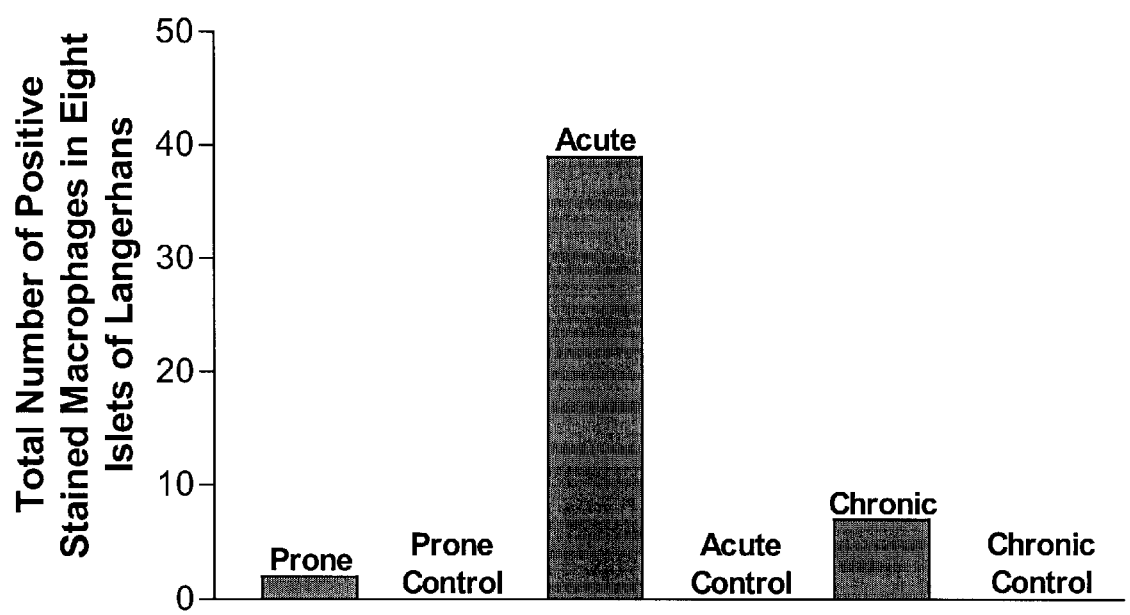
FIG. 16 is a bar graph that denotes the total number of positive stained tissue-activated rat macrophages in eight randomly counted islet cellular regions. Note the significant greater numbers of macrophages are present in the acute BBDP/W or rat pancreas.

The chronic-staged BBDP/Wor pancreas showed a reduced number of tissue-activated macrophages (FIG. 15a), compared to the acute model. The chronic aged-matched control (chronic BBDR/Wor) showed no evidence of macrophages in its pancreatic tissue section (FIG. 15b). FIG. 16 denotes a bar graph of the total number of pancreatic tissue-activated macrophages for all groups/stages.

Rodent tissue-activated macrophage counts were statistically computed from islet pancreatic regions and results were graphed using GraphPad Prism® program. Paired t test was used to compare each BBDP/Wor Type-1 stage to its appropriate control. There was a statistically significant difference of the total number of tissue-activated macrophages between the acute and chronic BBDP/Wor and their aged-matched controls (p=0.0003 and p=0.02, respectively). There was no statistically significant difference of the total number of tissue-activated macrophages between the prone BBDP/Wor and the aged-matched control (p=0.796). Tukey's Multiple Comparison Test was used to compared the total acute BBDP/Wor tissue-activated macrophage count to all other groups and there was a statistically significant difference (p value less than 0.001).

With these results, one aspect of this invention is a medical therapy that involves the administration of the PDE2 inhibitor (preferably also a PDE5 inhibitor) at the stage of Type I diabetes development when macrophage invasion is occurring. Macrophages release cytokines that can recruit other inflammatory cells such as lymphocytes and neutrophils, all of which can cause damage to islet cells. Thus, it is desirable to begin therapy at the stage of macrophage activation.

TABLE I

Quantitative Immunohistochemistry of PDE2 and PDE5 in Islet Cell Region

| Tissue Identification | Stage of Disease | Mean Number of Cells with Brown Intensity in Islet Cells (PDE2) | Mean Number of Cells with Brown Intensity in Islet Cells (PDE5) |
| --- | --- | --- | --- |
| B14A | Chronic Type-I | 85 ± 32.9 | 111 ± 14.5 |
| B14D | B14A age-matched resistant control | 71 ± 32.6 | 87 ± 7.2 |
| B14B | Acute Type-I | 56 ± 26.5 | 96 ± 6.8 |
| B14E | B14B age-matched resistant control | 78 ± 6.3 | 102 ± 8.5 |
| B14C | Prone Type-I | 58 ± 33.2 | 87 ± 6.4 |
| B14F | B14C age-matched resistant control | 57 ± 39.8 | 93 ± 4.9 |

TABLE II

Quantitative Immunohistochemistry of Positive Stained Macrophage in Islet Cell Region

| Tissue Identification | Stage of Disease | Total Number of Macrophages Per Six Pancreatic Islets |
| --- | --- | --- |
| B14A | Chronic Type-I | 7 |
| B14D | B14A age-matched resistant control | 0 |
| B14B | Acute Type-I | 39* |
| B14E | B14B age-matched resistant control | 0 |
| B14C | Prone Type-I | 2 |
| B14F | B14C age-matched resistant control | 0 |

*compared to other groups, p value less than 0.001

Human Pancreatic Tissue PDE Analysis in Type I Diabetes Patients

Human formalin-fixed paraffin-embedded 5-$\mu$m thick pancreatic tissue was obtained from a 22 year-old female and another female of unknown age. Both patients had a history of Type-I diabetes mellitus. A serial dilution study demonstrated the optimal signal-to-noise ratio was 1:100 and 1:200 (PDE2), 1:500 and 1:1000 (PDE5). Anti-PDE2 and anti-PDE5 antibodies were used as the primary antibodies, and the principal detection system consisted of a Vector anti-sheep secondary (BA-6000) and Vector ABC-AP Kit (AK-5000) with a Vector Red substrate kit (SK-5100), which was used to produce a fuchsia-colored red deposit. Tissues were also stained with a positive control antibody (CD31) to ensure the tissue antigens were preserved and accessible for immunohistochemical analysis. CD31 is present in monocytes, macrophages, granulocytes, B lymphocytes and platelets. The negative control consisted of performing the entire immunohistochemistry procedure on adjacent sections in the absence of primary antibody. Slides were imaged using a DVC Digital Photo Camera coupled to a Nikon microscope.

Figure 17A:
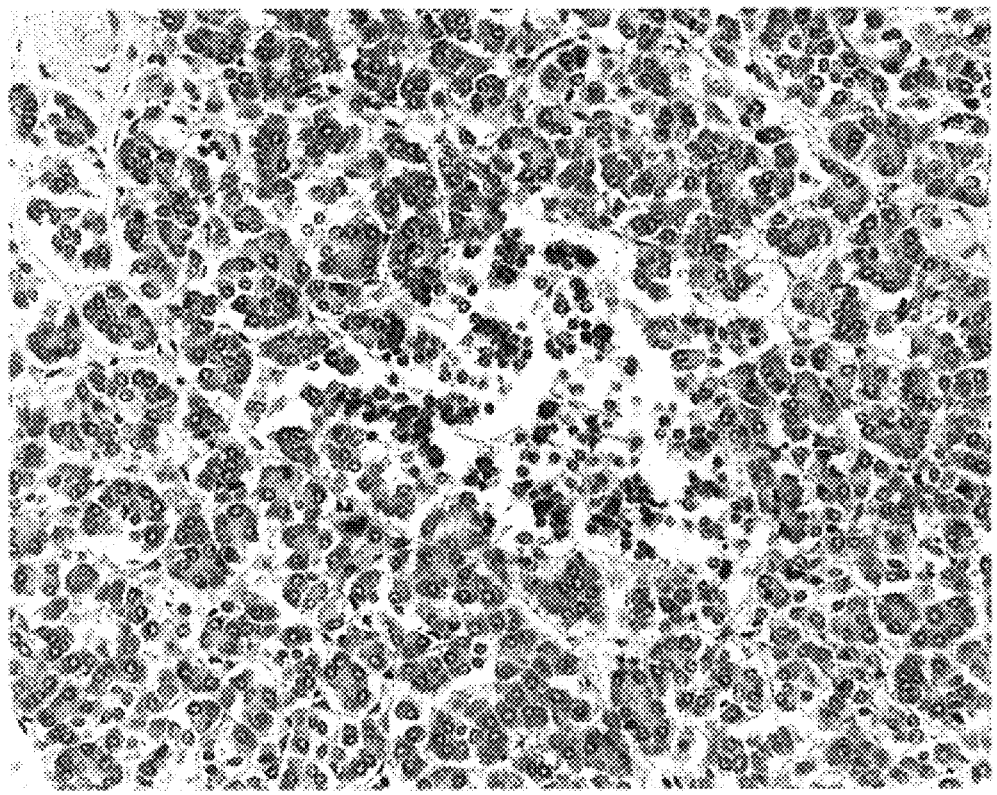
FIGS. 17a and 17b represent pancreatic tissue specimens from two human patients where the specimens are stained for PDE2 protein.
Figure 17B:
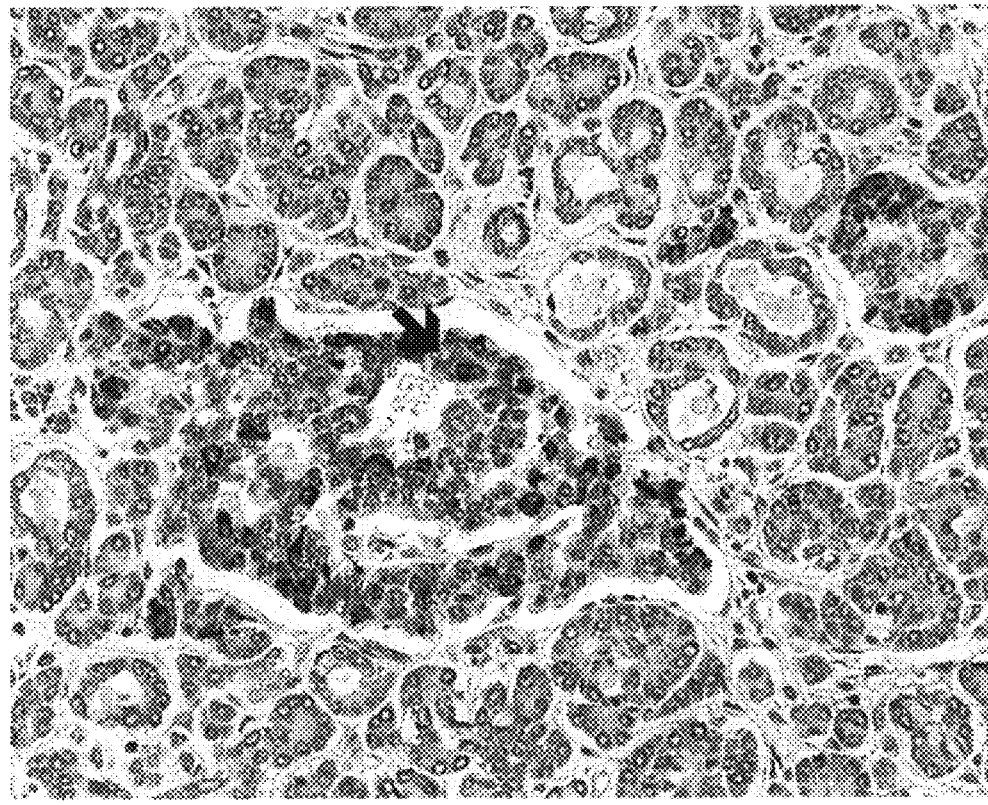
Figure 18A:
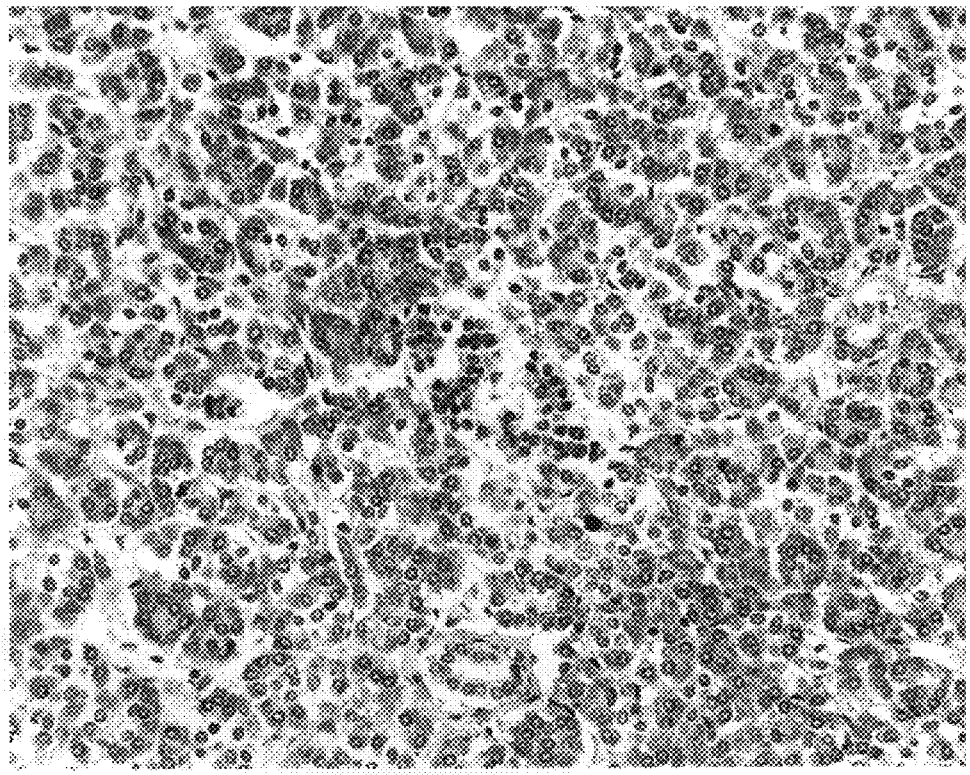
FIGS. 18a and 18b represent pancreatic tissue specimens from two human patients where the specimens are stained for PDE5 protein.
Figure 18B:
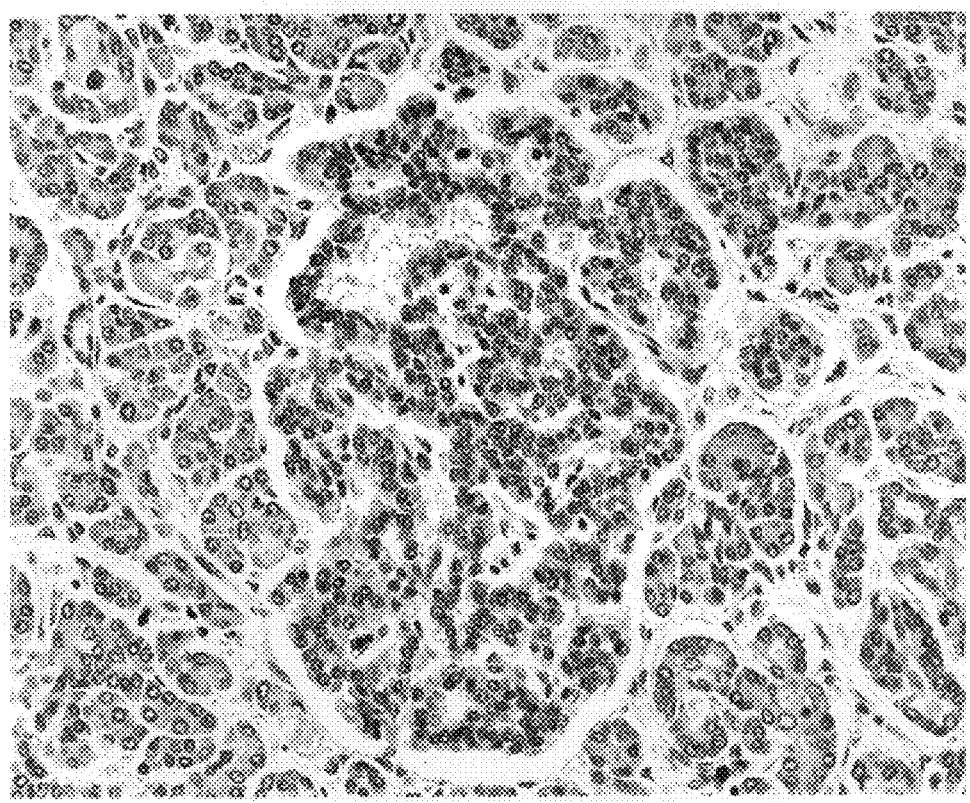

Human pancreatic tissue samples (1 and 2) exhibited positive staining for PDE2 and PDE5 proteins and immunostaining was mostly localized to pancreatic islet cells. In FIGS. 17a and 17b, pancreatic tissue specimens from the two human patients described above are stained for PDE2 protein. In FIGS. 18a and 18b pancreatic tissue specimens from the two human patients described above are stained for PDE5 protein.

FIG. 17b shows a positively stained macrophage overexpressing PDE5 protein (see arrow).

It will be understood that various changes and modifications can be made in the details of procedure, formulation and use without departing from the spirit of the invention, especially as defined in the following claims.

We claim:

1. A method of treating type I diabetes in a mammal with that disease comprising administering to the mammal a physiologically effective amount of an inhibitor of PDE2.

2. The method of claim 1 wherein mammal is also administered an inhibitor of PDE5.

3. The method of claim 2 wherein said inhibitor of PDE2 and PDE5 comprise the same compound.

4. The method of claim 1 wherein said inhibitor does not substantially inhibit COX I or COX II.

5. The method of claim 2 wherein said inhibitor does not substantially inhibit COX I or COX II.

6. The method of claim 5 wherein said inhibitor has an $IC_{50}$ for PDE2 of no more than about 25 $\mu$M. and has an $IC_{50}$ for each of the COX enzymes greater than about 40 $\mu$M.

7. A method of treating type I diabetes in a mammal comprising administering to the mammal a compound of the formula:

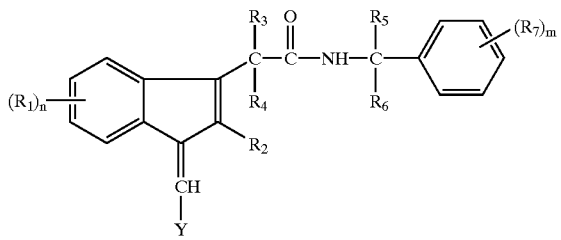

wherein $R^1$ is independently selected in each instance from the group consisting of hydrogen, halogen, lower alkyl, loweralkoxy, amino, loweralkylamino, di-loweralkylamino, loweralkylmercapto, loweralkyl sulfonyl, cyano, carboxamide, carboxylic acid, mercapto, sulfonic acid, xanthate and hydroxy;
- $R_2$ is selected from the group consisting of hydrogen and lower alkyl;
- $R_3$ is selected from the group consisting of hydrogen, halogen, amino, hydroxy, lower alkyl amino, and di-loweralkylamino;
- $R_4$ is hydrogen, or $R_3$ and $R_4$ together are oxygen;
- $R_5$ and $R_6$ are independently selected from the group consisting of hydrogen, lower alkyl, hydroxy-substituted lower alkyl, amino lower alkyl, lower alkylamino-lower alkyl, lower alkyl amino di-lower alkyl, lower alkyl nitrile, —$CO_2H$, —$C(O)NH_2$, and a $C_2$ to $C_6$ amino acid;
- $R_7$ is independently selected in each instance from the group consisting of hydrogen, amino lower alkyl, lower alkoxy, lower alkyl, hydroxy, amino, lower alkyl amino, di-lower alkyl amino, amino lower alkyl, halogen, —$CO_2H$, —$SO_3H$, —$SO_2NH_2$, and —$SO_2$(lower alkyl);
- m and n are integers from 0 to 3 independently selected from one another;
- Y is selected from the group consisting of quinolinyl, isoquinolinyl, pyridinyl, pyrimidinyl, pyrazinyl, imidazolyl, indolyl, benzimidazolyl, triazinyl, tetrazolyl, thiophenyl, furanyl, thiazolyl, pyrazolyl, or pyrrolyl, or substituted variants thereof wherein the substituents are one or two selected from the group consisting of halogen, lower alkyl, lower alkoxy, amino, lower alkylamino, di-lower alkylamino, hydroxy, —$SO_2$ (lower alkyl) and —$SO_2NH_2$; and pharmaceutically acceptable salts thereof.

8. The method of claim 7 wherein Y is selected from pyridinyl or quinolonyl.

9. The method of claim 7 wherein $R_1$ is selected from the group consisting of halogen, lower alkoxy, amino, hydroxy, lower alkylamino and di-loweralkylamino.

10. The method of claim 9 wherein $R^1$ is selected from the group consisting of halogen, lower alkoxy, amino and hydroxy.

11. The method of claim 7 wherein $R_2$ is lower alkyl.

12. The method of claim 10 wherein $R_2$ is lower alkyl.

13. The method of claim 7 wherein $R_3$ is selected from the group consisting of hydrogen, halogen, hydroxy, amino, lower alkylamino and di-loweralkylamino.

14. The method of claim 10 wherein $R_3$ is selected from the group consisting of hydrogen, halogen, hydroxy, amino, lower alkylamino and di-loweralkylamino.

15. The method of claim 14 wherein $R_3$ is selected from the group consisting of hydrogen, hydroxy and lower alkylamino.

16. The method of claim 14 wherein $R_3$ is selected from the group consisting of hydrogen, hydroxy and lower alkylamino.

17. The method of claim 7 wherein $R_5$ and $R_6$ are independently selected from the group consisting of hydrogen, hydroxy-substituted lower alkyl, amino lower alkyl, lower alkylamino-lower alkyl, lower alkyl amino di-lower alkyl, —$CO_2H$, —$C(O)NH_2$.

18. The method of claim 16 wherein $R_5$ and $R_6$ are independently selected from the group consisting of hydrogen, hydroxy-substituted lower alkyl, amino lower alkyl, lower alkylamino-lower alkyl, lower alkyl amino di-lower alkyl, —$CO_2H$, —$C(O)NH_2$.

19. The method of claim 7 wherein $R_5$ and $R_6$ are independently selected from the group consisting of hydrogen, hydroxy-substituted lower alkyl, lower alkyl amino di-lower alkyl, —$CO_2H$, —$C(O)NH_2$.

20. The method of claim 18 wherein $R_5$ and $R_6$ are independently selected from the group consisting of hydrogen, hydroxy-substituted lower alkyl, lower alkyl amino di-lower alkyl, —$CO_2H$, —$C(O)NH_2$.

21. The method of claim 7 wherein $R_7$ is independently selected in each instance from the group consisting of hydrogen, lower alkoxy, hydroxy, amino, lower alkyl amino, di-lower alkyl amino, halogen, —$CO_2H$, —$SO_3H$, —$SO_2NH_2$, amino lower alkyl, and —$SO_2$(lower alkyl).

22. The method of claim 20 wherein $R_7$ is independently selected in each instance from the group consisting of hydrogen, lower alkoxy, hydroxy, amino, lower alkyl amino, di-lower alkyl amino, halogen, —$CO_2H$, —$SO_3H$, —$SO_2NH_2$, amino lower alkyl, and —$SO_2$(lower alkyl).

23. The method of claim 7 wherein $R_7$ is independently selected in each instance from the group consisting of hydrogen, lower alkoxy, hydroxy, amino, halogen, —$CO_2H$, —$SO_3H$, —$SO_2NH_2$, amino lower alkyl, and —$SO_2$(lower alkyl).

24. The method of claim 19 wherein $R_7$ is independently selected in each instance from the group consisting of hydrogen, lower alkoxy, hydroxy, amino, halogen, —$CO_2H$, —$SO_3H$, —$SO_2NH_2$, amino lower alkyl, and —$SO_2$(lower alkyl).

25. The method of claim 23 wherein at least one of the $R_7$ substituents is ortho- or para-located.

26. She method of claim 24 wherein at least one of the $R_7$ substituents is ortho- or para-located.

27. The method of claim 25 wherein at least one of the $R_7$ substituents is ortho-located.

28. The method of claim 26 wherein at least one of the $R_7$ substituents is ortho-located.

29. The method of claim 7 wherein Y is selected from the group consisting of quinolinyl, isoquinolinyl, pyridinyl, pyrimidinyl and pyrazinyl or said substituted variants thereof.

30. The method of claim 7 wherein said compound comprises (Z)-5-fluoro-2-methyl-(4-pyridylidene)-3-(N-benzyl)indenylacetamide hydrochloride.

31. The method of claim 7 wherein said compound comprises (Z)-5-fluoro-2-methyl-(4-pyridylidene)-3-(N-benzyl)-indenylacetamide p-methylbenzenesulfonate.

32. A method of inhibiting activated macrophages in a mammal with type I diabetes comprising chronically administering to the mammal a physiologically effective amount of an inhibitor of PDE2.

33. The method of claim 32 wherein mammal is also administered an inhibitor of PDE5.

34. The method of claim 33 wherein said inhibitor of PDE2 and PDE5 comprise the same compound.

35. The method of claim 32 wherein said inhibitor does not substantially inhibit COX I or COX II.

36. The method of claim 34 wherein said inhibitor does not substantially inhibit COX I or COX II.

37. The method of claim 32 wherein the mammal is a companion pet.

38. The method of claim 37 wherein the mammal is human.

39. A method of treating type I diabetes in a mammal with that disease comprising inhibiting PDE2 in the diseased tissue without substantially inhibiting COX I or COX II.

40. A method of inhibiting activated macrophages in a mammal with type I diabetes comprising chronically administering to the mammal a physiologally effective amount of an inhibitor of PDE2 having a PDE2 $IC_{50}$ no more than about 25 $\mu$M and having a COX $IC_{50}$ greater than about 40 $\mu$M.

* * * * *